(12) United States Patent
Kada et al.

(10) Patent No.: US 6,713,221 B2
(45) Date of Patent: Mar. 30, 2004

(54) ESTER WAX AND TONER USING THE WAX

(75) Inventors: Koji Kada, Amagasaki (JP); Kouhei Sawada, Nishinomiya (JP); Show Onodera, Hanamaki (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 10/043,825

(22) Filed: Jan. 11, 2002

(65) Prior Publication Data

US 2002/0172879 A1 Nov. 21, 2002

(30) Foreign Application Priority Data

Jan. 12, 2001 (JP) ........................................ 2001-005761

(51) Int. Cl.⁷ ................................................ G03G 9/08
(52) U.S. Cl. ................................ 430/108.4; 430/108.8; 568/884; 554/170
(58) Field of Search ........................... 430/108.4, 108.8; 568/884; 554/170

(56) References Cited

U.S. PATENT DOCUMENTS

| | | | |
|---|---|---|---|
| 2,297,691 A | 10/1942 | Carlson | |
| 5,510,222 A | 4/1996 | Inaba et al. | |
| 5,635,325 A | 6/1997 | Inaba et al. | |
| 5,712,072 A | 1/1998 | Inaba et al. | |
| 5,741,617 A | 4/1998 | Inaba et al. | |

FOREIGN PATENT DOCUMENTS

| | | |
|---|---|---|
| JP | 43-24748 | 7/1965 |
| JP | 42-23910 | 8/1965 |
| JP | 52-3304 | 10/1972 |
| JP | 52-3305 | 10/1972 |
| JP | 57-52574 | 7/1973 |
| JP | 57-37353 | 8/1980 |
| JP | 63-66563 | 9/1986 |
| JP | 1-185660 | 1/1988 |
| JP | 1-185661 | 1/1988 |
| JP | 1-185662 | 1/1988 |
| JP | 1-185663 | 1/1988 |
| JP | 2949558 | 6/1994 |
| JP | 7-98511 | 4/1995 |
| JP | 8-50367 | 2/1996 |
| JP | 8-50368 | 2/1996 |
| JP | 8-297376 | 8/1996 |
| JP | 11-160909 | 11/1997 |
| JP | 2000-19768 | 6/1998 |
| JP | 2000-56505 | 8/1998 |

*Primary Examiner*—Mark A. Chapman
(74) *Attorney, Agent, or Firm*—Webb Ziesenheim Logsdon Orkin & Hanson, P.C.

(57) ABSTRACT

An ester wax is obtained by a condensation reaction of carboxylic acid and alcohol; wherein the carboxylic acid contains a single kind of saturated linear monocarboxylic acid having 14 to 30 carbon atoms as a main component, and the single kind of carboxylic acid is contained in a ratio of 60 wt % or more of the entire carboxylic acid; the alcohol contains a single kind of saturated linear monohydric alcohol having 14 to 30 carbon atoms or a single kind of polyhydric alcohol having 2 to 6 hydroxyl groups and having 2 to 30 carbon atoms as a main component, and when the monohydric alcohol is the main component, the monohydric alcohol is contained in a ratio of 60 wt % or more of the entire alcohol, and when the polyhydric alcohol is the main component, the polyhydric alcohol is contained in a ratio of 80 wt % or more of the entire alcohol; and the ester wax has an acid value of 3 mgKOH/g or less, and a hydroxyl value of 5 mgKOH/g or less, and a maximum peak temperature in a differential thermal curve is in a range from 55° C. to 90° C.

17 Claims, 22 Drawing Sheets

ESTER WAX AND TONER USING THE WAX

BACKGROUND OF THE INVENTION

1. Field of the Invention

The present invention relates to an ester wax used preferably in development of electrostatically charged images formed by electrophotography or electrostatic recording in a copier, a laser printer, etc, and to toner containing the wax.

2. Description of the Prior Art

The electrophotography technique used in copiers for business use or the like has been developed based on the electrophotography technique described in U.S. Pat. No. 2,297,691, Japanese Patent Publication (Tokko) Nos. 42-23910 and 43-24748. Electrophotography is a technique for forming visible images from image information via electrostatic latent images. More specifically, this technique includes the steps of attaching resin powder containing colored fine powder to electrostatic latent images formed on a photoreceptor to form toner images, transferring the toner images on a recording medium such as paper or OHP sheets, and fixing the toner images thereon by heating, pressing or other methods for a long time or semi-permanent fixation.

In recent years, high speed, compactness, color image formation, and low temperature fixation have been in demand for copiers, and in order to meet this demand, not only improvements in the apparatus of a copier but also a high performance toner for the apparatus have been in demand. In order to meet the requirements of energy saving laws that will be enacted in the future, the fixing temperature should be lowered to reduce power consumption of the entire apparatus, in particular, to reduce power consumption of a fixing apparatus, which is a challenge that should be inevitably achieved. From the viewpoint of prevention of environmental pollution, it is desirable that production of sublimates during heating is suppressed.

Recently, as a fixing process that can meet the above requirement, a roller fixing method that has good heat efficiency and can be realized in a compact mechanism or a flash fixing method that can be performed with high speed are used preferably.

However, in the flash fixing method, toner is momentarily subjected to a high temperature, so that more sublimates can be generated. In a heated roller fixing method, the surface of a heated roller is brought in contact with toner images on a paper sheet, and therefore a so-called offset phenomenon occurs in which toner is attached onto the surface of the heated roller, and transferred to a subsequently supplied recording medium, staining the images.

In order to prevent the offset phenomenon in the heated roller method, Japanese Laid-Open Patent Publication No. 57-37353 proposes use of a polyester resin having a three-dimensional network structure as a resin contained in toner. However, this kind of polyester resin includes unreacted hydroxyl groups or carboxyl groups in a molecule of the resin, so that if copying is repeated, the charge amount of the toner may vary significantly with ambient humidity. Therefore, a reduction of the image density or image staining such as a fog are caused, so that sufficient reliability cannot be obtained. Furthermore, Japanese Patent Publication (Tokko) Nos. 52-3304 and 52-3305, and Japanese Patent Publication No. 57-52574 propose a method for improving the releasing properties of the toner by blending polyethylene, polypropylene or the like as a releasing agent in the toner. However, if the toner contains these releasing agents, the melting point of the toner is increased, so that if fixation is performed at low fixing temperatures, a sufficient fixing strength on transfer paper cannot be obtained.

Another attempt is to use natural wax to improve the characteristics of the toner. For example, Japanese Laid-Open Patent Publication Nos. 1-185660, 1-185661, 1-185662, and 1-185663 propose a method of internally adding carnauba wax or montan wax to toner. However, these waxes usually contain free alcohols or free fatty acids in an amount of 10 wt % or more, and further contain a resin or a colored component, so that they do not have sharp melting characteristics. In particular, a component that melts at 55° C. or less is present in the waxes, so that the surface portion of the toner is partially melted under storage conditions and in an environment for use, and thus, blocking of the toner occurs. In addition, the toner to which such ester wax is internally added has insufficient melting properties when heat is applied and has insufficient color reproducibility when original images are copied. The colored component present in the above-described waxes deteriorates the color reproducibility on OHP sheets, so that the toner containing such a wax cannot sufficiently meet the requirement of high image quality. Furthermore, in a flash fixing method, sublimates derived from impurities contained in the wax are produced during a fixing process, so that environmental pollution may be caused.

In recent years, instead of carnauba wax or montan wax, synthetic waxes having uniform quality and good supply stability have received attention. Japanese Laid-Open Patent Publication Nos. 7-98511, 8-50367, 8-50368, 8-297376, 11-160909, 2000-19768, and 2000-56505 and Japanese Patent Publication No. 2949558 use an ester compound obtained from a monohydric alcohol or polyhydric alcohol and saturated linear fatty acid as a wax for toner.

When synthesizing an ester, in order to minimize the acid value in the final product, alcohol has to be used excessively, and consequently, a raw material alcohol remains in the final product. On the other hand, in order to minimize the hydroxyl value, a fatty acid has to be used excessively, and consequently, a raw material fatty acid remains in the final product.

As described above, the synthetic ester waxes described in the above publications contain a raw material fatty acid or a raw material alcohol and further contain a catalyst for synthesis, so that they do not exhibit a sharp melting behavior. If toner contains such a synthetic ester wax, the anti-blocking properties, the storage stability and the anti-offset properties of the toner are insufficient. Furthermore, during toner kneading, the raw material fatty acid and the raw material alcohol in the wax are subjected to oxidation degradation, so that problems such as discoloring of the toner itself and odor generation are caused. Moreover, components produced by degradation of the raw material fatty acid and the raw material alcohol turn into sublimates, so that a filter for capturing them is clogged in a shorter time.

As described above, the conventional ester wax for toner does not act sufficiently as a releasing agent for toner, and is not sufficiently satisfactory in terms of reliability.

SUMMARY OF THE INVENTION

The present invention provides a synthetic ester wax that contains only a small amount of a raw material fatty acid and a raw material alcohol and has a sharp melting characteristic.

The present invention further provides toner containing the above ester wax so that it has anti-blocking properties and storage stability, and excellent color reproducibility, fixing properties and anti-offset properties.

As a result of in-depth study on the above-described problems, the inventors of the present invention found that since an ester wax that is synthesized by the use of a monocarboxylic acid and a monohydric or polyhydric alcohol having a specific number of carbon atoms and that has specific chemical properties has a sharp thermal melting behavior, the anti-blocking properties and the anti-offset properties can be improved and sublimates can be reduced by using this ester wax for toner, and thus the present invention has been attained.

An ester wax of the present invention is obtained by a condensation reaction of carboxylic acid and alcohol; wherein the carboxylic acid contains a single kind of saturated linear monocarboxylic acid having 14 to 30 carbon atoms as a main component, and the single kind of carboxylic acid is contained in a ratio of 60 wt % or more of the entire carboxylic acid; the alcohol contains a single kind of saturated linear monohydric alcohol having 14 to 30 carbon atoms or a single kind of polyhydric alcohol having 2 to 6 hydroxyl groups and having 2 to 30 carbon atoms as a main component, and when the monohydric alcohol is the main component, the monohydric alcohol is contained in a ratio of 60 wt % or more of the entire alcohol, and when the polyhydric alcohol is the main component, the polyhydric alcohol is contained in a ratio of 80 wt % or more of the entire alcohol; and the ester wax has an acid value of 3 mgKOH/g or less and a hydroxyl value of 5 mgKOH/g or less, and a maximum peak temperature in a differential thermal curve is in a range from 55° C. to 90° C.

In a preferred embodiment, in the differential thermal curve of the ester wax, 80% or more of a total peak area lies in a 10° C. range between the maximum peak temperature minus 7° C. and the maximum peak temperature plus 3° C.

In a preferred embodiment, in the differential thermal curve of the ester wax, a peak area corresponding to a temperature region of ¾ on the low temperature side of a peak area in a range from a melting start temperature to the maximum peak temperature is 35% or less of the total peak area.

In a preferred embodiment, a half band width of the maximum peak in the differential thermal curve of the ester wax is 5° C. or less.

An ester wax of the present invention is obtained by a process comprising a condensation reaction of carboxylic acid and alcohol; wherein the carboxylic acid contains a single kind of saturated linear monocarboxylic acid having 14 to 30 carbon atoms as a main component, and the single kind of carboxylic acid is contained in a ratio of 60 wt % or more of the entire carboxylic acid; the alcohol contains a single kind of saturated linear monohydric alcohol having 14 to 30 carbon atoms or a single kind of polyhydric alcohol having 2 to 6 hydroxyl groups and having 2 to 30 carbon atoms as a main component, and when the monohydric alcohol is the main component, the monohydric alcohol is contained in a ratio of 60 wt % or more of the entire alcohol, and when the polyhydric alcohol is the main component, the polyhydric alcohol is contained in a ratio of 80 wt % or more of the entire alcohol; and the process comprises adding a hydrocarbon solvent to an esterified crude product obtained by the condensation reaction in a ratio of 5 to 100 parts by weight with respect to 100 parts by weight of the esterified crude product; and performing neutralization with an aqueous alkali solution.

In a preferred embodiment, the ester wax is obtained by a process comprising further adding an alcohol solvent having 1 to 3 carbon atoms in a ratio of 3 to 50 parts by weight with respect to 100 parts by weight of the esterified crude product, in addition to the hydrocarbon solvent, and performing neutralization with an aqueous alkali solution.

An ester wax of the present invention is obtained by a process comprising a condensation reaction of carboxylic acid and alcohol; wherein the carboxylic acid contains a single kind of saturated linear monocarboxylic acid having 14 to 30 carbon atoms as a main component, and the single kind of carboxylic acid is contained in a ratio of 60 wt % or more of the entire carboxylic acid; the alcohol contains a single kind of saturated linear monohydric alcohol having 14 to 30 carbon atoms or a single kind of polyhydric alcohol having 2 to 6 hydroxyl groups and having 2 to 30 carbon atoms as a main component, and when the monohydric alcohol is the main component, the monohydric alcohol is contained in a ratio of 60 wt % or more of the entire alcohol, and when the polyhydric alcohol is the main component, the polyhydric alcohol is contained in a ratio of 80 wt % or more of the entire alcohol; and the process comprises adding a water-soluble organic solvent to an esterified crude product obtained by the condensation reaction in a ratio of 3 to 50 parts by weight with respect to 100 parts by weight of the esterified crude product, and performing neutralization with an aqueous alkali solution; wherein the water-soluble organic solvent has a boiling point that is a temperature exceeding a melting temperature of the esterified crude product but not more than 300° C., and has a specific gravity of 0.9 or more.

The present invention also includes a toner that comprises 100 parts by weight of a binding resin and 0.1 to 40 parts by weight of the above-mentioned ester wax.

Thus, the present invention described herein makes it possible to achieve the objects of (i) providing an ester wax that is obtained from a specific monocarboxylic acid and a specific alcohol and has specific thermal properties and chemical characteristics so that it can be used suitably in various fields; (ii) providing an ester wax that can be used preferably in a display device such as rewritable card and rewritable paper utilizing changes in the properties such as the optical transparency and the fluidity of the wax due to heat; a material for controlling electrical resistance in a thermo-sensor; a releasing material used in thermal transfer film; an adhesive that can effect peeling and adhesion repeatedly by changing the temperature; a developing material as typified by toner and the like; (iii) providing a toner containing the ester wax, in which blocking does not occur during storage so that it has excellent storage stability; and (iv) providing a toner that has excellent fixing properties, anti-offset properties and color reproducibility, good optical transparency of images fixed on an OHP film, and provides long term reliability to a copier, a printer or the like.

DETAILED DESCRIPTION OF THE INVENTION

Figure 1:
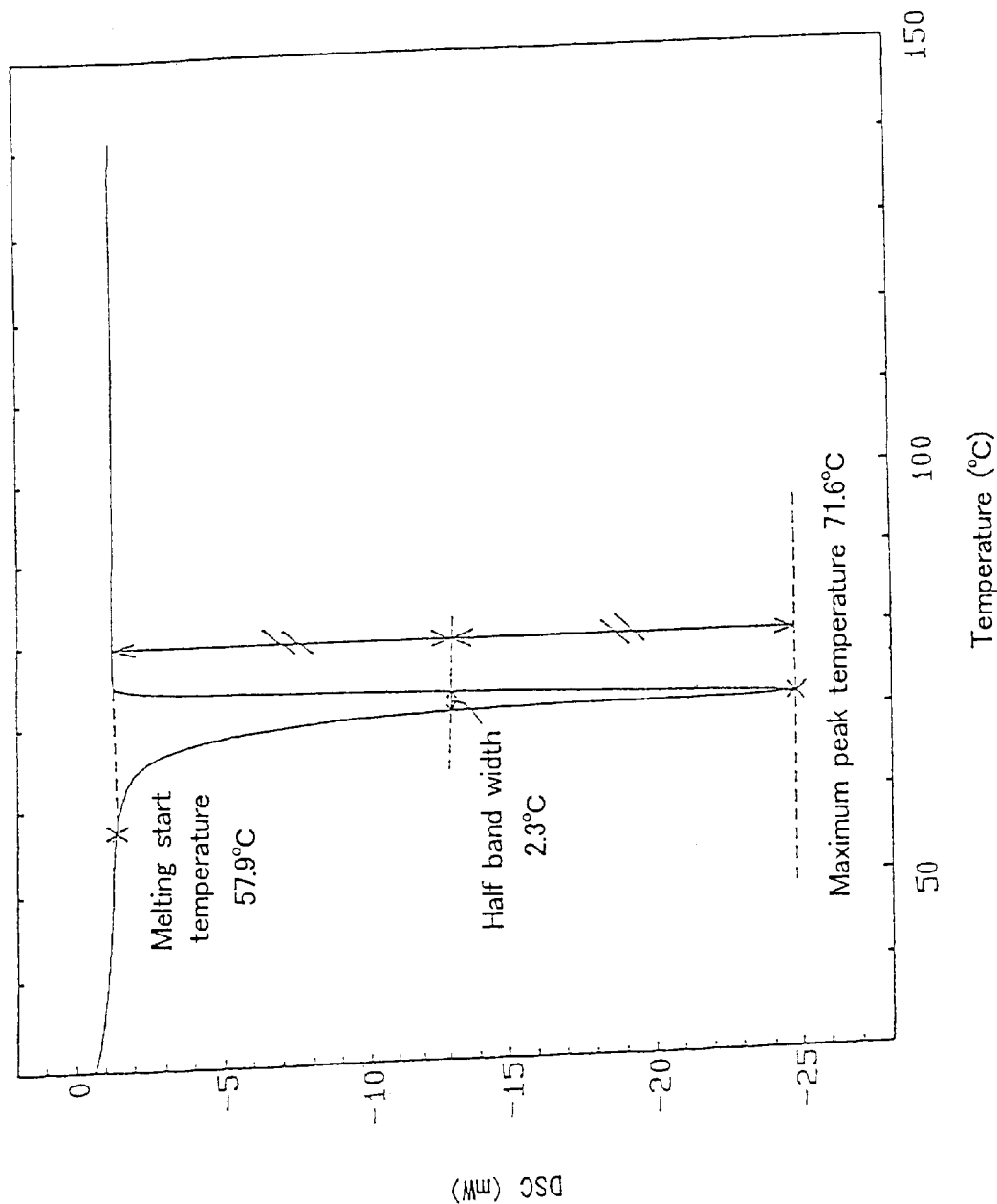
FIG. 1 is a chart showing a differential thermal curve of a typical ester wax.

Hereinafter, the present invention will be described in detail.

The ester wax of the present invention is an ester compound obtained from carboxylic acid (hereinafter also referred to as component a) and alcohol (hereinafter also referred to as component b). The carboxylic acid (component a) contains a single kind of saturated linear monocarboxylic acid having 14 to 30 carbon atoms as a main component, and the carboxylic acid that is the main component is contained in a ratio of 60 wt % or more of the entire carboxylic acid (i.e., the total amount of the component a). The alcohol (component b) contains a single kind of saturated linear monohydric alcohol (component b1) having 14 to 30 carbon atoms or a single kind of polyhydric alcohol (component b2) having 2 to 6 hydroxyl groups and having 2 to 30 carbon atoms as a main component. When the monohydric alcohol (component b1) is the main component, the monohydric alcohol is contained in a ratio of 60 wt % or more of the entire alcohol (i.e., the total amount of the component b). When the polyhydric alcohol (component b2) is the main component, the polyhydric alcohol is contained in a ratio of 80 wt % or more of the entire alcohol (i.e., the total amount of the component b).

Examples of the saturated linear monocarboxylic acid include myristic acid, palmitic acid, stearic acid, arachic acid, behenic acid, lignoceric acid, cerotic acid, montanoic acid, and melissic acid.

Examples of the saturated linear monohydric alcohol (component b1) include myristyl alcohol, cetyl alcohol, stearyl alcohol, arachyl alcohol, behenyl alcohol, tetracosanol, hexacosanol, octacosanol, and triacontanol.

Among the polyhydric alcohols having 2 to 6 hydroxyl groups (component b2) examples of alcohols having 2 hydroxyl groups include ethylene glycol, propylene glycol, 1,3-propane diol, 1,4-butane diol, 1,5-pentane diol, 1,6-hexane diol, 1,10-decane diol, 1,12-dodecane diol, 1,14-tetradecane diol, 1,16-hexadecane diol, 1,18-octadecane diol, 1,20-eicosane diol, 1,30-triacontane diol, diethylene glycol, dipropylene glycol, 2,2,4-trimethyl-1,3-pentane diol, neopentyl glycol, 1,4-cyclohexane dimethanol, spiroglycol, 1,4-phenylene glycol, bisphenol A, and hydrogenated bisphenol A. Examples of alcohols having 3 hydroxyl groups include 1,2,4-butane triol, 1,2,5-pentane triol, 2-methyl-1,2,4-butane triol, glycerin, 2-methylpropane triol, trimethylolethane, triethylolethane, trimethylolpropane, and 1,3,5-trihydroxy methyl benzene. Examples of alcohols having 4 hydroxyl groups include 1,2,3,6-hexane tetrol, and pentaerythritol. Examples of alcohols having 5 hydroxyl groups include glucose. Examples of alcohols having 6 hydroxyl groups include dipentaerythritol.

When the ester wax of the present invention is obtained from the above-described saturated linear monocarboxylic acid and a saturated linear monohydric alcohol, it is preferable that the total number of carbon atoms of the ester is 36 or more in view of the anti-blocking properties and the storage stability of toner containing the ester wax. The number of carbon atoms is more preferably 40 or more, and particularly preferably 44 or more.

In view of thermal melting behavior (sharp melting characteristics) of the ester wax, for the saturated linear monocarboxylic acid that is a raw material of the ester wax of the present invention, it is preferable that the total content of the above-mentioned single kind of saturated linear monocarboxylic acid (i.e., a main component of the component a) and a saturated linear monocarboxylic acid having up to two carbon atoms more or less than the main component is 60 wt % or more. This content is more preferably 80 wt % or more, even more preferably 90 wt % or more, particularly preferably 95 wt % or more, and most preferably 98 wt % or more. In a more preferable embodiment of the content of the carboxylic acid, the above-mentioned single kind of saturated linear monocarboxylic acid itself is contained in a ratio of 60 wt % or more. This content is more preferably 80 wt % or more, even more preferably 90 wt % or more, and most preferably 95 wt % or more.

Also for the saturated linear monohydric alcohol (component b1) of the alcohol (component b) that is a raw material of the ester wax, it is preferable that the total content of the saturated linear monohydric alcohol that is a main component of the alcohol and an alcohol having up to two carbon atoms more or less than the main component of the alcohol is 60 wt % or more. This content is more preferably 80 wt % or more, even more preferably 90 wt % or more, particularly preferably 95 wt % or more, and most preferably 98 wt % or more. In a more preferable embodiment of the content of the alcohol, the main component of the alcohol is contained in a ratio of 60 wt % or more. This content is more preferably 80 wt % or more, even more preferably 90 wt % or more, and most preferably 95 wt % or more.

Regarding the polyhydric alcohol (component b2) having 2 to 6 hydroxyl groups, it is preferable that the polyhydric alcohol that is a main component of the alcohol is contained in a ratio of 80 wt % or more. This content is more preferably 85 wt % or more, even more preferably 90 wt % or more, and most preferably 95 wt % or more.

In the ester wax of the present invention, the maximum peak temperature of the differential thermal curve is in the range of 55° C. to 90° C. The maximum peak temperature is the temperature at which the amount of absorbed heat is the maximum in the differential thermal curve obtained by the differential scanning calorimetry (DSC). For example, the maximum peak temperature in the differential thermal curve of FIG. 1 is 71.6° C. If an ester wax having a maximum peak temperature of less than 55° C. is used, for example, for toner, blocking readily occurs in the toner box and an aggregate is formed during storage. Thus, the toner has poor storage stability. When the maximum peak temperature exceeds 90° C., the fixing properties are deteriorated.

The ester wax of the present invention has an acid value of 3 mgKOH/g or less. The acid value is preferably 2 mgKOH/g or less, more preferably 1 mgKOH/g or less, and particularly preferably 0.5 mgKOH/g or less. The hydroxyl value of the ester wax of the present invention is 5 mgKOH/g or less. The hydroxyl value is preferably 4 mgKOH/g or less, more preferably 3 mgKOH/g or less, and particularly preferably 2 mgKOH/g or less. If the acid value exceeds 3 mgKOH/g, or if the hydroxyl value exceeds 5 mgKOH/g, various problems are caused, for example, when this ester wax is used for a resin for toner. More specifically, the following problems are caused: during fixation, due to residual alcohol and residual fatty acid, the generation of volatile substances increases, the melting start temperature is lowered, or a sharp thermal melting behavior is hardly obtained (the endothermic peak derived from impurities increases in the differential thermal curve).

It is preferable that the ester wax of the present invention has such a sharp thermal melting behavior that 80% or more of the total peak area lies in the 10° C. range between the maximum peak temperature minus 7° C. and the maximum peak temperature plus 3° C.

Figure 3:
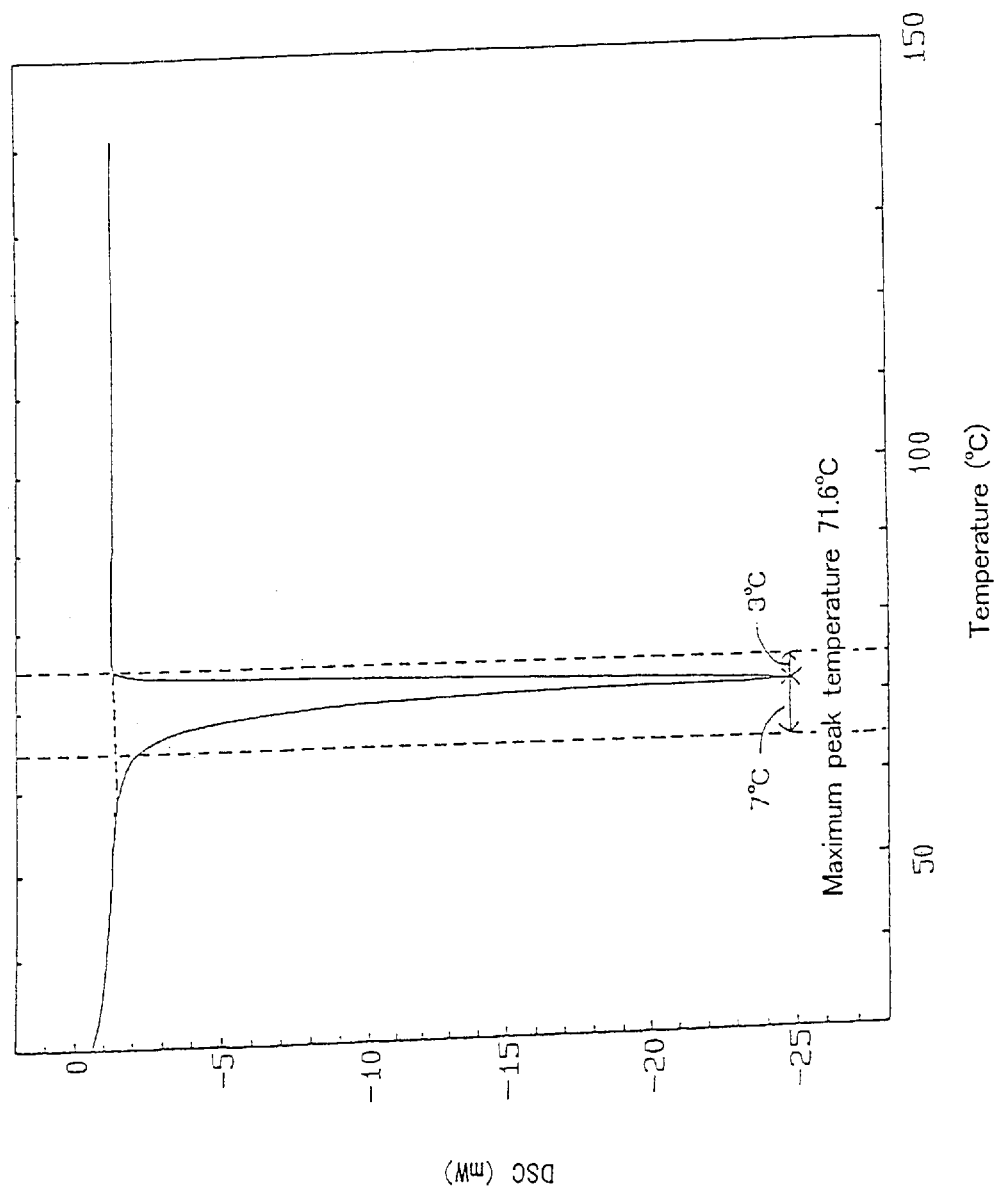
FIG. 3 is a chart showing a differential thermal curve of a typical ester wax.

Herein, "total peak area" refers to the area defined by the following two lines in the differential thermal curve: a line obtained by extending the base line on the high temperature side to the low temperature side; and the differential thermal curve. "Area included in the 10° C. range between the maximum peak temperature minus 7° C. and the maximum peak temperature plus 3° C." refers to the area defined by the following four lines when vertical lines (parallel to the vertical axis) are drawn from the temperature axis at 7° C. on the low temperature side from the maximum peak temperature and 3° C. on the high temperature side from the maximum peak temperature: the base line of the differential thermal curve (including the extended line obtained by extending the base line on the high temperature side in the differential thermal curve to the low temperature side; this applies also to the following description); the vertical line on the high temperature side; the vertical line on the low temperature side; and the differential thermal curve. In the differential thermal curve of FIG. 3, 98.0% of the total peak area is included in the above-described temperature range of 10° C. including the maximum peak. When an ester wax whose peak area included in the above-described temperature range of 10° C. including the maximum peak is less than 80% of the total peak area is internally added to a toner, the toner has problems such as poor anti-offset properties and poor fixing properties.

Figure 2:
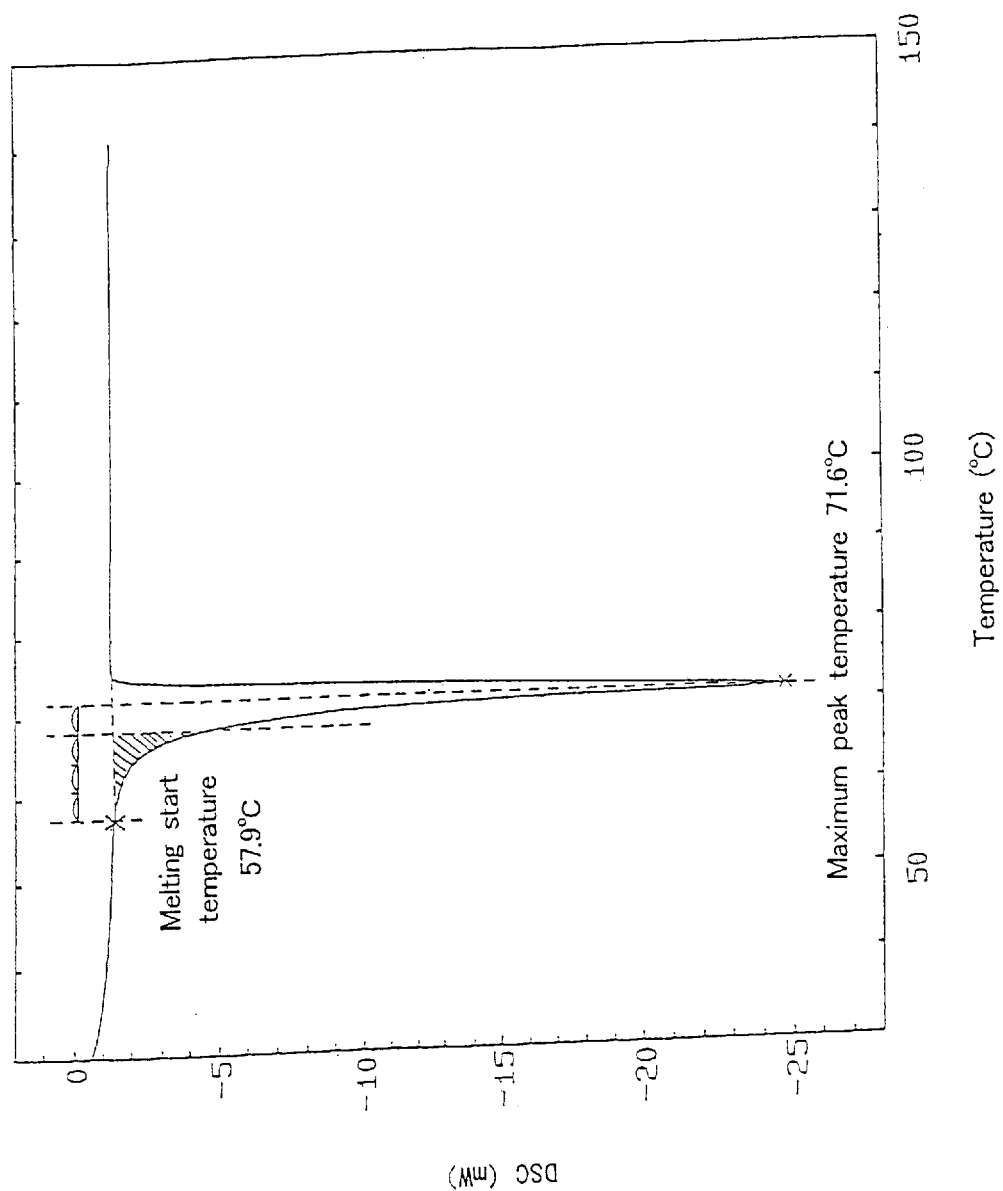
FIG. 2 is a chart showing a differential thermal curve of a typical ester wax.

In the ester wax of the present invention, it is preferable that the peak area included in the temperature region of ¾ on the low temperature side of the peak area in the range from the melting start temperature to the maximum peak temperature is 35% or less of the total peak area. This ratio is more preferably 30% or less, and particularly preferably 25% or less. The ester wax having such a differential thermal curve has a sharp thermal melting behavior. Herein, "peak area in the range from the melting start temperature to the maximum peak temperature" refers to the area defined by the following three lines: a vertical line drawn from the maximum peak of the differential thermal curve to the base line of the curve; the base line; and the differential thermal curve on the low temperature side from the vertical line. "Peak area included in the temperature region of ¾ on the low temperature side" refers to the area defined by the following three lines: a vertical line drawn at the temperature corresponding to ¾ on the low temperature side in the temperature range from the melting start temperature to the maximum peak temperature from the temperature axis; the differential thermal curve on the low temperature side from the vertical line; and the base line. In the differential thermal curve of FIG. 2, the peak area corresponding to the temperature region of ¾ on the low temperature of the peak area in the range from the melting start temperature to the maximum peak temperature is 13.0%. If an ester wax in which that area exceeds 35% is used for a toner, a low temperature melting component is partially melted during storage, so that toner particles are aggregated, and thus blocking may be caused in a toner box.

In the ester wax of the present invention, it is preferable that the half band width at the maximum peak is 5° C. or less. The half band width is more preferably 4° C. or less, more preferably 3.5° C. or less, and particularly preferably 3° C. or less. Herein, the half band width refers to the temperature width of the peak of the differential thermal curve at ½ of the height (peak height) of a vertical line from the maximum point to the base line. For example, in the differential thermal curve of FIG. 1, the half band width is 2.3° C. When an ester wax whose half band width exceeds 5° C. is internally added to a toner, the toner has the following problem: when heat from a fixing roll is instantly applied to the toner during high speed copying the melting properties of the wax in the toner particles become non-uniform, the fixing properties are deteriorated, and sufficient image stability cannot be obtained.

In the ester wax of the present invention, it is preferable that the melting start temperature is 50° C. or more. Herein, "melting start temperature" refers to the temperature at the intersection of the differential thermal curve and the extended line of the base line on the high temperature side from the maximum peak to the low temperature side. For example, in the differential thermal curve of FIG. 1, the melting start temperature is 57.9° C. When the melting start temperature is lower than 50° C., the toner to which such an ester wax is internally added has the problem that the toner particles are aggregated readily during storage so that blocking occurs.

The Vickers hardness of the ester wax of the present invention is preferably 2 or more, and more preferably 4 or more. When pressure is applied to toner containing such an ester wax, the toner particles are hardly broken and hardly attached to each other, and thus the toner has excellent anti-blocking properties.

In the ester wax of the present invention, it is preferable that the color number (APHA) during melting is 300 or less, more preferably 250 or less, even more preferably 200 or less and most preferably 150 or less in view of color reproduction.

In the ester wax of the present invention, it is preferable that in the thermogravimetry (TG), when the temperature is increased at 250° C./min at a nitrogen flow of 200 ml/min, the temperature at which the weight decrease due to heating reaches 0.5 wt % is 290° C. or more, in view of the thermal stability and the reduction of low temperature sublimates.

In the ester wax of the present invention, it is preferable that the penetration at 50° C. (measured according to the penetration test method of JIS K 2235) is 2 or less, more preferably 1 or less, and most preferably 0.5 or less in view of the storage stability.

In the ester wax of the present invention, it is preferable that the melt viscosity at 100° C. is 100 mPa·s or less, more preferably 80 mPa·s or less, even more preferably 60 mPa·s or less, and most preferably 40 mPa·s or less in view of the fixing properties and the anti-offset properties. The viscosity here is measured with a Brookfield rotational viscometer.

In order to obtain the ester wax of the present invention, for example, first, the above-described alcohol (component b) and an excessive amount of carboxylic acid (component a) are used to effect an esterification reaction (condensation reaction). The reaction is performed in the presence or the absence of a catalyst and generally at 120 to 240° C. Such an esterification reaction provides an esterified crude product.

Next, the excessive carboxylic acid (component a) in the esterified crude product is removed by neutralization with an aqueous alkali solution. Examples of the aqueous alkali solution used for the neutralization include aqueous solutions of alkali metal salts such as sodium hydroxide, potassium hydroxide, sodium carbonate, potassium carbonate, and sodium hydrogencarbonate and ammonium salts such as ammonium carbonate. In general, an aqueous alkali solution with a concentration of 5 to 20 wt % can be used. The amount of the alkali is preferably 1 to 2 equivalents of the acid value of the esterified crude product obtained by reacting the carboxylic acid and the alcohol.

The ester wax of the present invention that has the maximum peak of the differential thermal curve in the specific range and has an acid value and a hydroxyl value in predetermined ranges can be selected from the thus obtained ester waxes.

The ester wax of the present invention can be obtained easily by adding a specific organic solvent during neutralization with an aqueous alkali solution of the esterified crude product obtained by an esterification reaction of the carboxylic acid (component a) and the alcohol (component b). This organic solvent is a hydrocarbon solvent (solvent I) or a water-soluble organic solvent (solvent II) having the properties described below. Using these specific organic solvents, more satisfactory layer separation can be accomplished during washing with water.

Examples of the hydrocarbon solvent (solvent I) include toluene, xylene, cyclohexane, and normal heptane. When the hydrocarbon solvent (solvent I) is used, the amount of the solvent added is preferably 5 to 100 parts by weight with respect to 100 parts by weight of the esterified crude product. An amount of less than 5 parts by weight may lead to poorly separated layers or an emulsified state. Even if the amount exceeds 100 parts by weight, there is no improvement corresponding to the addition amount and on the contrary, the process for removing the solvent may take a long time so that the productivity may be deteriorated.

In addition to the hydrocarbon solvent (solvent I), if alcohol having 1 to 3 carbon atoms (alcohol for separation) is added in a ratio of 3 to 30 parts by weight, preferably 5 to 30 parts by weight with respect to 100 parts by weight of the esterified crude product, even more satisfactory layer separation can be accomplished. Examples of such an alcohol for separation include methanol, ethanol, normal propanol, and isopropanol.

The water-soluble organic solvent (solvent II) has a boiling point that is a temperature higher than the melting temperature of the esterified crude product but not more than 300° C., and has a specific gravity of 0.9 or more.

As described above, the water-soluble organic solvent (solvent II) has a boiling point that is a temperature higher than the melting temperature of the esterified crude product but not more than 300° C., more preferably a temperature higher than the melting temperature of the esterified crude product but not more than 250° C. When the boiling point of the water-soluble organic solvent is a temperature lower than the melting temperature of the esterified crude product, the solvent evaporates during washing with water, so that satisfactory layer separation may not be retained during neutralization/washing with water. On the other hand, if the boiling point is higher than 300° C., the water-soluble organic solvent is not removed sufficiently and remains in the ester. Therefore, it may be difficult to remove a trace amount of the remaining water-soluble organic solvent completely under reduced pressure in a subsequent process.

It is preferable that the water-soluble organic solvent (solvent II) used in the present invention has a specific gravity of 0.9 or more, as described above. When a water-soluble organic solvent having a specific gravity of less than 0.9 is used, the difference in the specific gravity between the desired ester and the water-soluble organic solvent is small, and therefore an organic layer containing the ester may not be separated from an aqueous layer containing the solvent during neutralization/washing with water.

The viscosity of this water-soluble organic solvent (solvent II) is preferably 30 mPa·s or less at a temperature for washing with water. When a water-soluble organic solvent having a viscosity higher than 30 mPa·s is used, the rate of separation into layers during neutralization/washing with water is reduced, and a distinguished interface between separated layers cannot be obtained, so that the neutralization and water-washing process may not be performed efficiently.

The above-described water-soluble organic solvent (solvent II) is added in a ratio of 3 to 50 parts by weight with respect to 100 parts by weight of the esterified crude product. When the water-soluble organic solvent is added in a ratio lower than 3 parts by weight, the resultant mixture may be emulsified, so that neutralization/washing with water may not be performed satisfactorily. When the water-soluble organic solvent is added in a ratio more than 50 parts by weight, satisfactory layer separation can be accomplished during neutralization, but the number of times of washing of an ester with water after the neutralization may be increased or it may be difficult to completely remove the water-soluble organic solvent remaining in the ester after washing under reduced pressure. From the above-described aspects, it is preferable that the amount of the water-soluble organic solvent actually used is the smallest possible amount that is sufficient to maintain satisfactory layer separation during neutralization.

Examples of the water-soluble organic solvent (solvent II) include ethylene glycol (boiling point: 198° C., specific gravity=1.11, viscosity at 90° C.: 2.5; hereinafter, the figures in parentheses following the solvent name indicate the boiling point, the specific gravity and the viscosity at 90° C.), ethylene glycol monomethyl ether (124° C., 0.97, 0.6), ethylene glycol monoethyl ether (135° C., 0.93, 0.6), ethylene glycol monoisopropyl ether (140° C., 0.91, 0.7), diethylene glycol monomethyl ether (194° C., 1.03, 0.6), diethylene glycol monobutyl ether (230° C., 0.96, 0.6), diethylene glycol dimethyl ether (160° C., 0.94, 0.5), propylene glycol (188° C., 1.04, 3.5), propylene glycol monomethyl ether (120° C., 0.92, 0.6), propylene glycol monoethyl ether (132° C., 0.90, 0.6), dipropylene glycol monomethyl ether (190° C., 0.95, 1.0), methoxy methoxy ethanol (168° C., 1.04, 0.5), ethylene glycol monoacetate (188° C., 1.11, 0.6), propylene glycol monoacetate (183° C., 1.06, 0.6), 1,3-butane diol (207° C., 1.01, 0.8), 2,3-butane diol (182° C., 1.01, 0.7), 1,4-butane diol (235° C., 1.02, 0.8), glycerin (290° C., 1.26, 2.2), glycerin-α-monomethyl ether (220° C., 1.11, 0.6), and glycerin-α, β-dimethyl ether (180° C., 1.02, 0.6). Particularly preferable are ethylene glycol, ethylene glycol monomethyl ether, ethylene glycol monoethyl ether, diethylene glycol monomethyl ether, propylene glycol, propylene glycol monomethyl ether, propylene glycol monoethyl ether, dipropylene glycol monomethyl ether, and the like. These solvents can be used alone or in combination of two or more. The water-soluble organic solvent (solvent II) can be used with the hydrocarbon solvent (solvent I). When the water-soluble organic solvent (solvent II) is used alone, no inflammable hydrocarbon solvent is used, so that the working environment advantageously can be kept safe.

Neutralization is performed by mixing the esterified crude product, the hydrocarbon solvent (solvent I) or the water-soluble organic solvent (solvent II) and an aqueous alkali solution, and an optional alcohol for separation (used in combination with the solvent I) to neutralize the acid present in the esterified crude product with the alkali. In general, neutralization is performed by mixing them sufficiently. The neutralization is performed while maintaining a temperature higher than the melting temperature of the esterified crude product. It is generally 50 to 100° C., preferably 70 to 90° C. When the temperature is lower than 50° C., layer separation may be poor or the mixture may be emulsified. When it exceeds 100° C., the ester may be hydrolyzed.

According to the neutralization, an organic layer (ester layer) containing the ester and an aqueous alkali layer separate from each other, and therefore this aqueous alkali layer is removed. Then, the ester layer is washed with warm water or hot water (50 to 100° C.). The washing is repeated until the washing waste water is substantially neutral (for example, the pH is about 7 or less). The solvents such as the solvent I or II and an optional alcohol for separation can be removed from the ester layer by repeatedly washing after neutralization. Furthermore, the solvent remaining in the ester after washing can be removed completely under a reduced pressure. Thus, the desired ester wax can be obtained.

If the above-described method is used, a high quality ester can be produced in a high yield without causing poor separation into layers and emulsification during neutralization. The thus obtained ester wax hardly contains a low volatile material, the raw material alcohol, the raw material carboxylic acid, an ester having a hydroxyl group or the like, and exhibits sharp melting characteristics. Therefore, it can be used effectively for a releasing agent for toner.

The toner of the present invention contains the above-described ester wax in a ratio of 0.1 to 40 parts by weight with respect to 100 parts by weight of a binding resin. Examples of the binding resin include a styrene resin, a polyolefin resin, an acrylic resin, and a polyester resin. The amount of the ester wax is preferably 0.1 to 20 parts by weight, and more preferably 1 to 10 parts by weight. When the mixing ratio is less than 0.1 parts by weight, the low temperature fixing properties and the anti-offset properties cannot be improved. On the other hand, when it exceeds 40 parts by weight, drum filming may occur. The toner can contain a single kind of ester wax of the present invention or a combination of two or more ester waxes of the present invention.

In the present invention, the toner can be used for either dry development or wet development. Usually, a binding resin having a softening point of about 80 to 200° C. is used. Specific examples thereof include a styrene resin, a polyolefin resin, an acrylic resin, and a polyester resin. These resins can be used alone or in combination of two or more.

The toner of the present invention can contain various additives in addition to the binding resin and the ester wax. Examples of the additives include other types of waxes, an abrasive, a fluidity providing agent, an anti-caking agent, and a conductivity providing agent such as carbon black and tin oxide. The additives optionally can be contained within the range that cannot impair the inherent advantages of the ester wax of the present invention.

The toner of the present invention can be either a monochrome toner or a color toner, and may contain a coloring agent, depending on the application of the toner. As the coloring agent, commonly used pigments or dyes can be used.

When the toner of the present invention is used as a two-component system developer, it can be used in combination with a carrier. In this case, commonly used carriers can be used. For example, magnetic powder such as iron powder, ferrite powder, and nickel power; glass beads; and these powders or beads whose surfaces are treated with a resin or the like can be used. The toner of the present invention can also be a one-component system magnetic toner containing a magnetic material.

Visible images produced on an image supporter with the toner are transferred to a recording medium, and then the toner is fixed on the recording medium by a commonly used fixing method, for example, by a contactless heating fixing method such as an open fixing method and a flash fixing method, a heating and pressing fixing method by the use of an elastic or rigid contact roller, and a fixing method employing these methods in combination. The heating temperature can be selected in accordance with the fixing speed or the quality of the paper. If the toner of the present invention is used, fixing can be performed with a lower energy than when conventional toners are used. Also when a contact type fixing apparatus is used, the anti-offset properties are good, and the material with which the contact type fixing apparatus is formed can be selected from a wider range.

An image forming apparatus that can use the toner of the present invention can be either a monochrome image forming apparatus or a color image forming apparatus, and can be either a dry or wet type image forming apparatus and can employ any conventional developers such as two-component system developers, magnetic one-component system developers, and non-magnetic one-component developers.

The ester wax of the present invention can be obtained from a specific carboxylic acid (component a) and a specific alcohol (component b), and has specific thermal properties and chemical characteristics. Such an ester wax has sharp melting characteristics, so that it is preferable as an ester wax used for a developing material such as a toner; a display device such as a rewritable card and rewritable paper utilizing changes in the properties such as the optical transparency and the fluidity of the wax due to heat; a material for controlling electrical resistance in a thermo-sensor; a releasing material used in thermal transfer film; an adhesive that can effect peeling and adhesion repeatedly by changing the temperature. In particular, if it is used for toner, blocking does not occur in the toner during storage, and thus the toner has excellent storage stability. This toner has excellent fixing properties, anti-offset properties and color reproducibility, and provides images fixed on an OHP film with good optical transparency.

EXAMPLES

Hereinafter, production examples of the ester wax of the present invention and methods for producing toners using these ester waxes will be described to explain the present invention more specifically. However, the present invention is not limited thereto. In the examples, "parts" means parts by weight.

The methods for evaluation used in the example of the present invention are as follows:

(1) Acid value of ester wax: based on JOCS 2.3.1-96
(2) Hydroxyl value of ester wax: based on JOCS 2.3.6.2-96
(3) Color number (APHA method, during melting) of ester wax: JOCS 2.2.1.4-96
(4) Viscosity (B type viscosity) of ester wax: the viscosity (mPa·s) measured at 100° C. with a Brookfield rotational viscometer.
(5) Hardness of ester wax: measured with a hardness measuring apparatus "Shimazu Dynamic ultrasmall hardness measuring apparatus DUH-W201S" manufactured by Shimadzu Cooperation. Measurement was performed with a Vickers indenter under a load of 4.9 mN, a load rate of 0.0948 mN/sec, a retention time of 15 sec, and a measurement temperature of 25° C., and dents formed on a cylindrical solid sample with a diameter of 20 mm and a thickness of 5 mm were analyzed to obtain the Vickers hardness.
(6) Measurement of heat characteristics of ester wax by differential scanning calorimetry: "SSC-5000" manufactured by Seiko Electronic Industries Co., Ltd. was used as the differential scanning calorimeter. The measurement was performed by placing about 10 mg of a wax sample in a sample holder and using 10 mg of alumina as the reference material. Differential thermal analysis was performed when the temperature was increased from 30° C. to 150° C. at 2° C./min.
(7) Evaluation of thermal stability of ester wax by thermogravimetry (TG): "TG/DTA220" manufactured by Seiko Electronics Industries Co., Ltd. was used as the apparatus for thermogravimetry. The measurement was performed by placing about 10 mg of a wax sample in a sample holder and using 10 mg. of alumina as the reference material. The weight decrease of the ester wax due to heating was measured when the temperature was increased at 250° C./min for two minutes under a nitrogen flow of 200 ml/min. The temperature at which the weight of the ester wax is decreased by 0.5 wt % was obtained and this was employed as the evaluation basis for the thermal stability.
(8) Storage stability of toner: The toner was placed in an air-tight container, and allowed to stand in a thermostatic chamber at 50° C. for 24 hours, and then the toner was removed and passed through a 60 mesh filter. If the weight ratio (%) of the toner after passing through the filter was 95% or more of the total weight of the toner, the storage stability of the toner was regarded as good.

(9) OHP optical transparency of images printed with a toner: The fixing temperature of a printer was set at 150° C., and printing was performed on a commercially available OHP ("Transparency" manufactured by Uchida Yoko Co., Ltd.) sheet. When light is applied to this OHP sheet, it was visually determined whether or not the printed portion transmits light. In the OHP transparency in Table 4, the symbol ○ indicates that light is transmitted, and the symbol X indicates that light is not transmitted.
(10) Fixing properties of toner: Images were printed with a commercially available monochrome copier (LBP404G manufactured by Canon Inc.) for a one-component toner, and a commercially available color copier OJTACHI HT-455 1-11) for a two-component toner. The fixing properties of the toner were evaluated in the following manner. An adhesive tape (Scotch mending tape manufactured by Sumitomo 3M Ltd.) was attached onto the surface of copied images, and a 500 g weight with a diameter of 5 cm was put thereon and was allowed to stand for 1 minute. Then, the tape was removed at a constant speed, and the attachment state onto the tape was visually observed for evaluation of the fixing properties. In the fixing properties in Table 4, the symbol ○ indicates that there is no attachment on the tape so that the fixing properties are good, and the symbol X indicates that there is much attachment on the tape so that the fixing properties are poor.
(11) Offset properties of toner: The offset properties were evaluated at the same time with the images printed for evaluation of the fixing properties of the toner by visually observing whether or not blank portions were stained with the toner. In the "offset" in Table 4, "absent" indicates that there is no toner stain, and "present" indicates that there are toner stains.
(12) Presence or absence of filming during copying: It was visually observed whether or not filming occurred at the time when 50,000 copies were made by using the above-described commercially available copiers.

I. Production and Evaluation of Ester Wax

Example 1

First, 100.0 g (0.734 mol) of pentaerythritol as the alcohol (component b) and 809.1 g (3.155 mol) of palmitic acid A (see Table 3) as the carboxylic acid (component a) were placed in a four-necked flask equipped with a thermometer, a nitrogen inlet, a stirrer and a condenser. Then, a reaction was carried out at an atmospheric pressure for 15 hours while distilling formed water at 220° C. under a nitrogen flow. Table 3 shows carbon numbers of carboxylic acids or alcohols contained in the titled materials and contents (wt %) of each of the carboxylic acids or alcohols in the materials. Table 3 also shows the raw material alcohol and the raw material carboxylic acid used in the examples and comparative examples described below. The amount of the obtained esterified crude product was 845.2 g, and the acid value of the product was 10.5 mgKOH/g. Then, 169.0 g of toluene and 53.2 g of ethanol (20 parts by weight of the hydrocarbon solvent and 6 parts by weight of the alcohol solvent for separation with respect to 100 parts by weight of the esterified crude product) were added to the esterified crude product. Then, a 10% potassium hydroxide aqueous solution containing potassium hydroxide in an amount corresponding to 1.5 equivalents of the acid value of the esterified crude product was added thereto, and the mixture was stirred at 70° C. for 30 minutes and then allowed to stand for 30 minutes. Then, an aqueous layer was removed, and thus the neutralization process was completed. Thereafter, ion exchanged water in a ratio of 20 parts by weight with respect to 100 parts by weight of the esterified crude product was added and the mixture was stirred at 70° C. for 30 minutes and allowed to stand for 30 minutes, followed by separation and removal of an aqueous layer. Washing was repeated four times with water until the pH of the waste water became neutral. The remaining ester layer was subjected to distillation to remove the solvent at 180° C. at a reduced pressure of 1 kPa and subjected to filtration so that an ester wax having a melting point of 71.6° C., an acid value of 0.2 mgKOH/g, and a hydroxyl value of 0.8 mgKOH/g was obtained in an amount of 786.0 g. The yield of the resultant ester from the esterified crude product that was supplied for neutralization was 93.0%.

Table 1 shows the names and the amounts (mole number) of the carboxylic acid (component a) and the alcohol (component b) used in this example, the initial ratio of the carboxyl groups and the hydroxyl groups thereof when the carboxylic acid and alcohol are provided for the esterification reaction, the amount and the hydroxyl value of the obtained esterified crude product, the names and the amounts of the aqueous alkali solution used for neutralization, the names and the amount of the organic solvent used for neutralization, the temperature for neutralization and water-washing, and the state of separation during neutralization and water-washing. The symbol ○ in the state of separation indicates that the state of separation is good. Table 1 also shows the data of the examples and the comparative examples described later.

Figure 4:
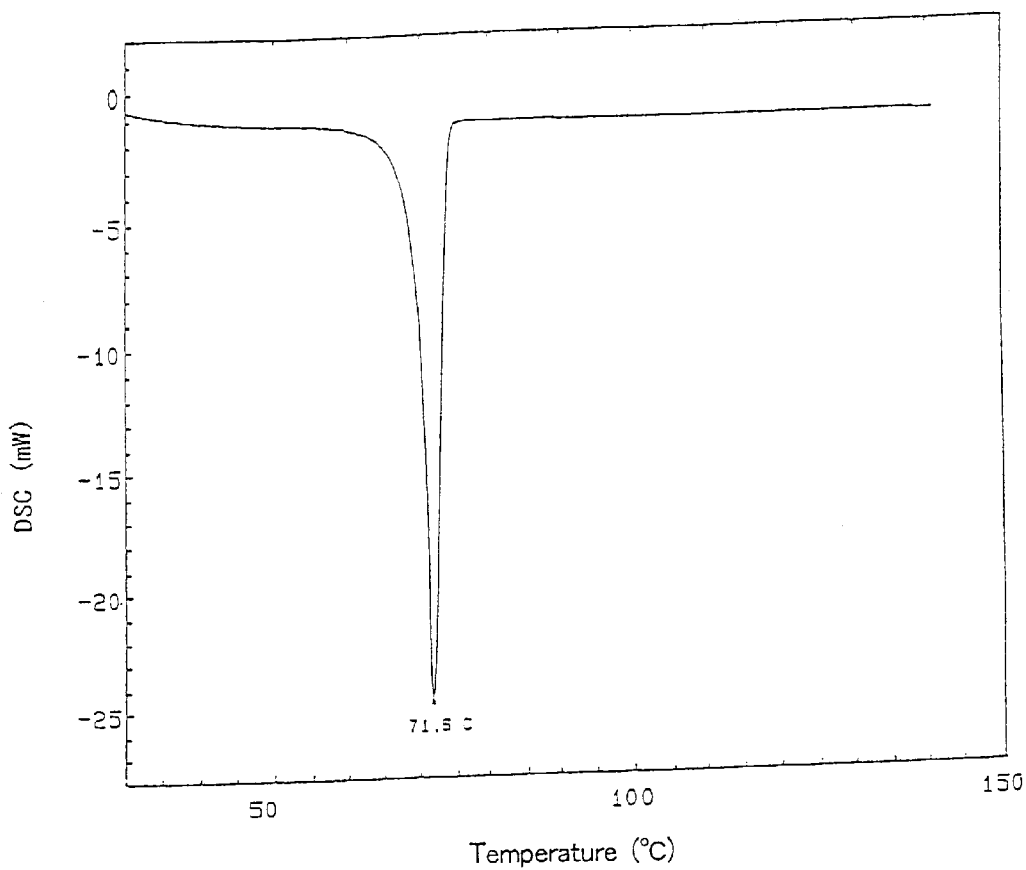
FIG. 4 is a chart showing a differential thermal curve of an ester wax obtained in Example 1.
Figure 5:
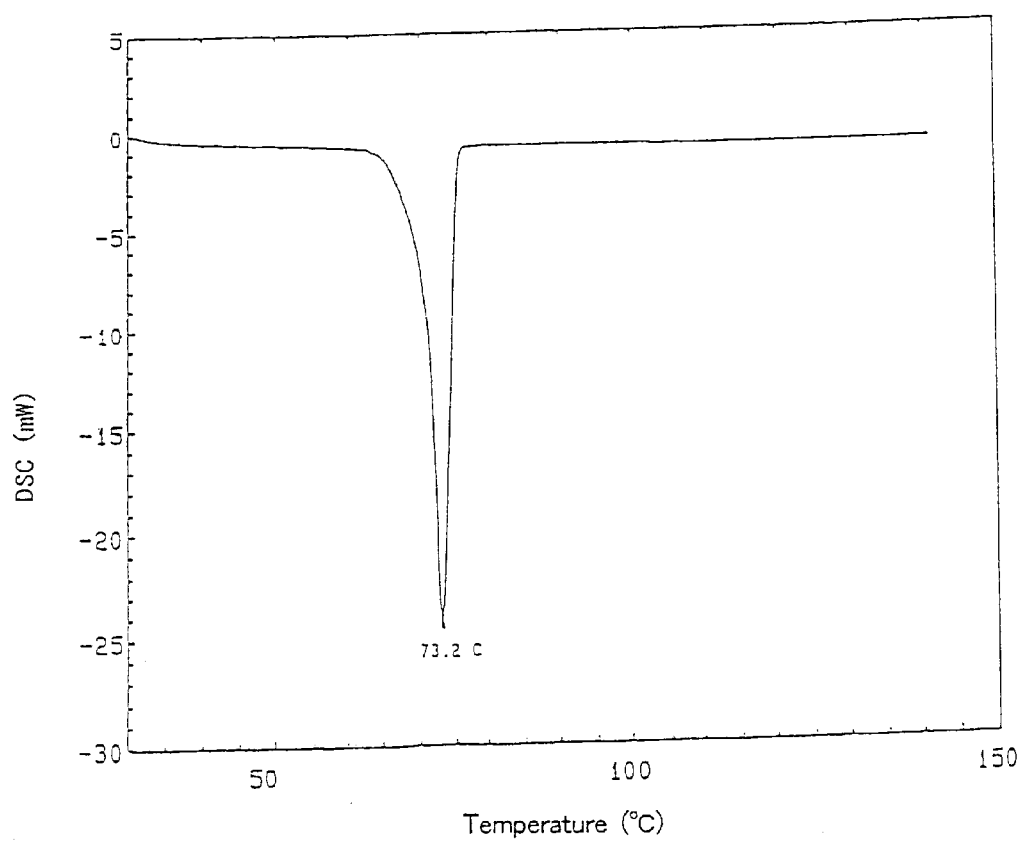
FIG. 5 is a chart showing a differential thermal curve of an ester wax obtained in Example 2.
Figure 6:
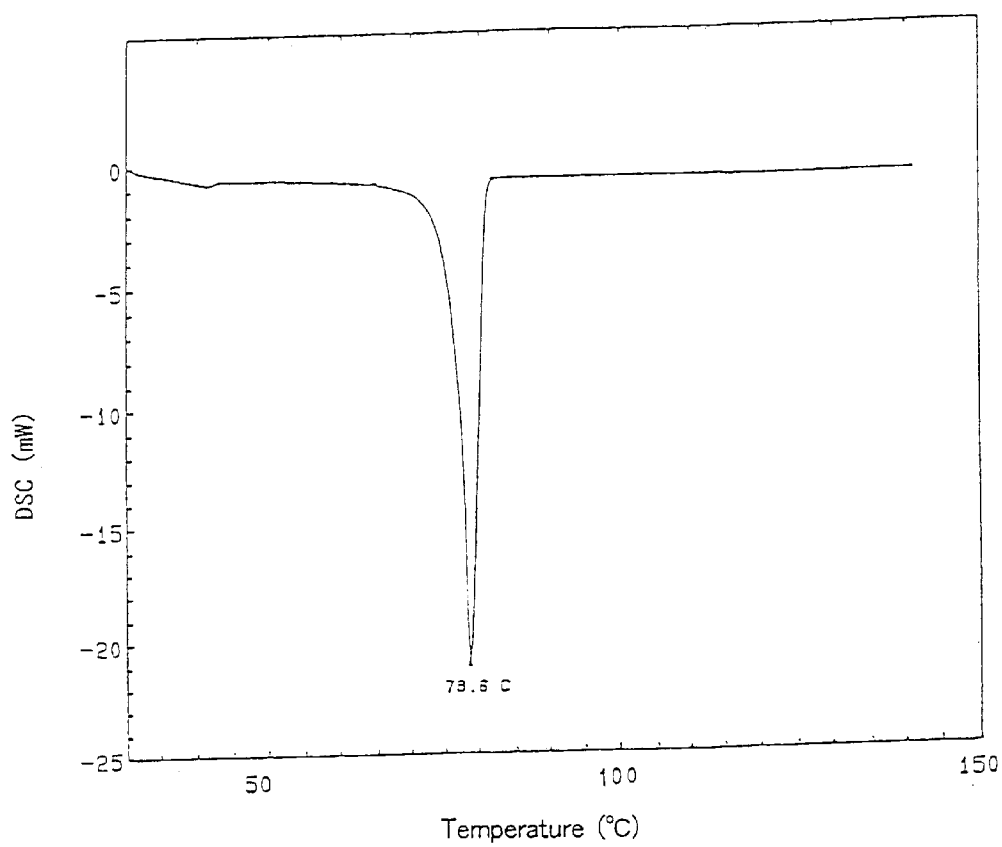
FIG. 6 is a chart showing a differential thermal curve of an ester wax obtained in Example 3.
Figure 7:
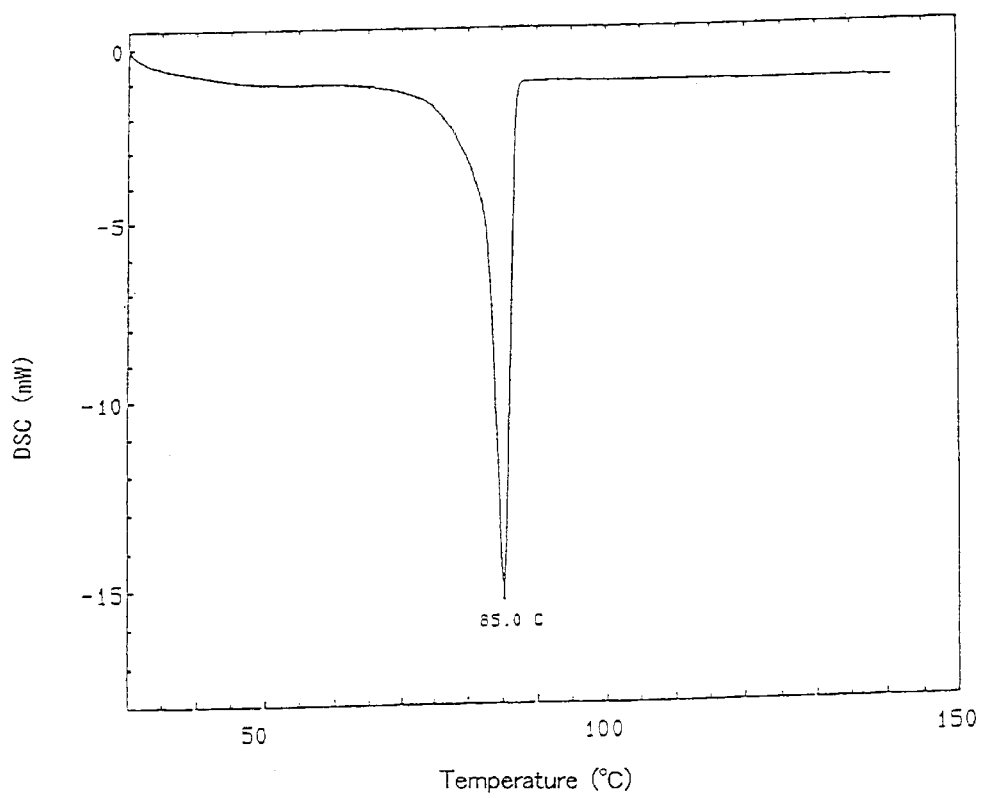
FIG. 7 is a chart showing a differential thermal curve of an ester wax obtained in Example 4.
Figure 8:
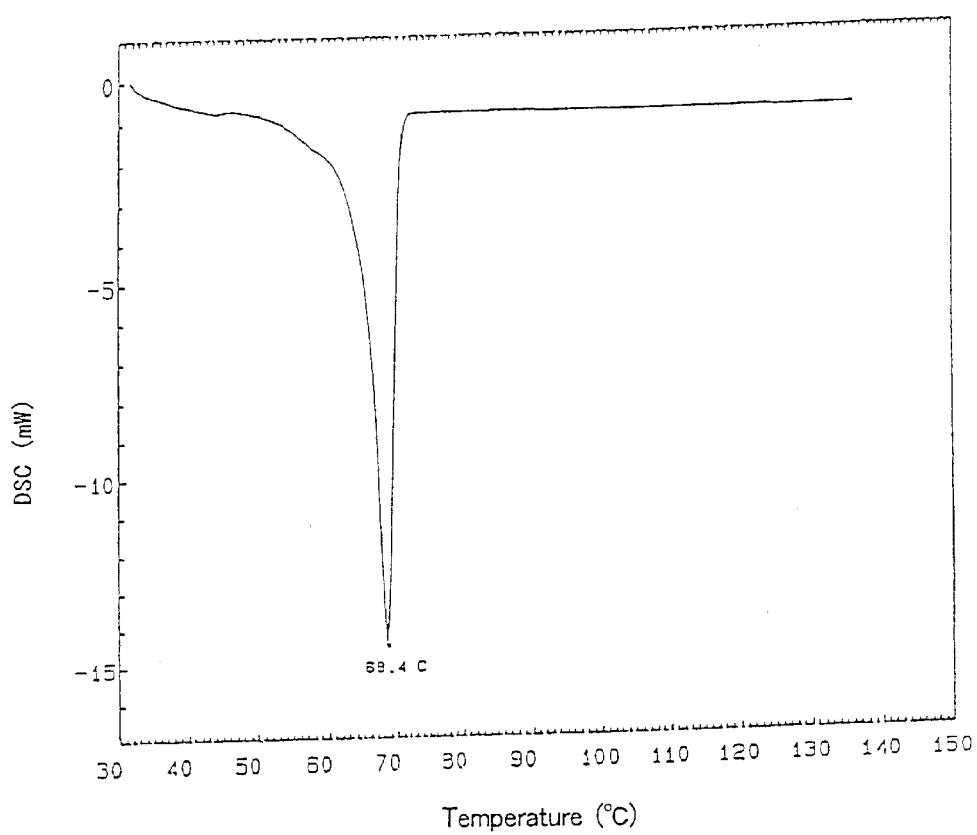
FIG. 8 is a chart showing a differential thermal curve of an ester wax obtained in Example 7.
Figure 9:
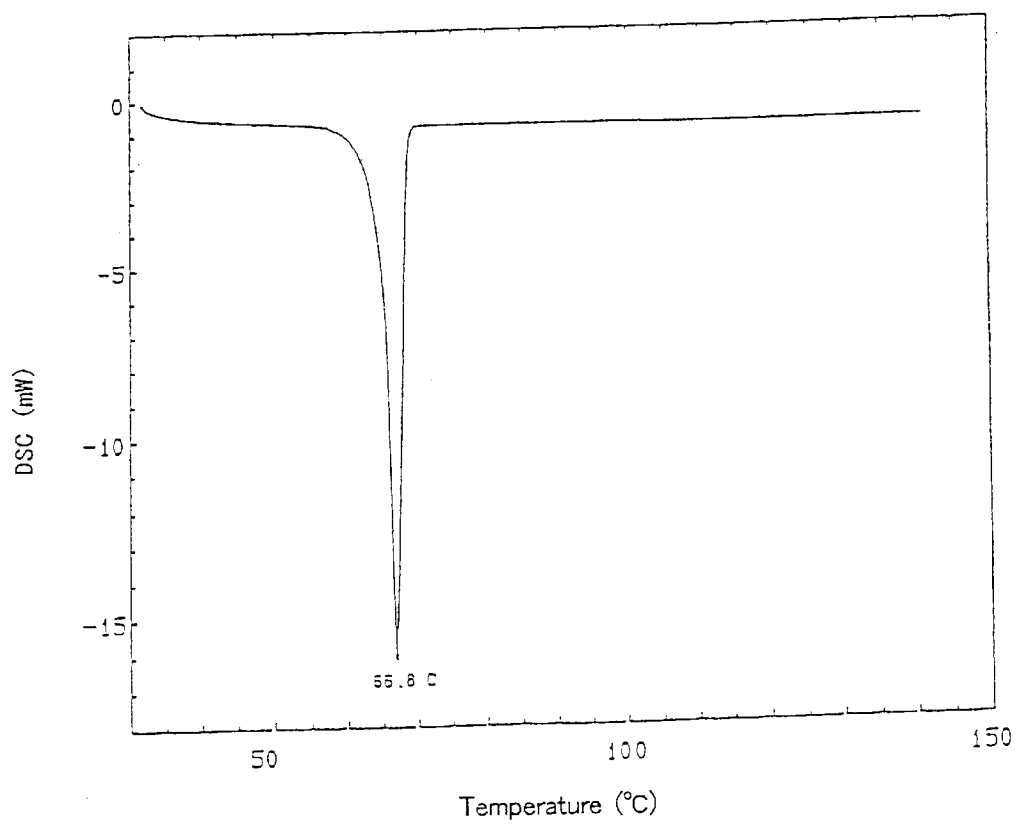
FIG. 9 is a chart showing a differential thermal curve of an ester wax obtained in Example 8.
Figure 10:
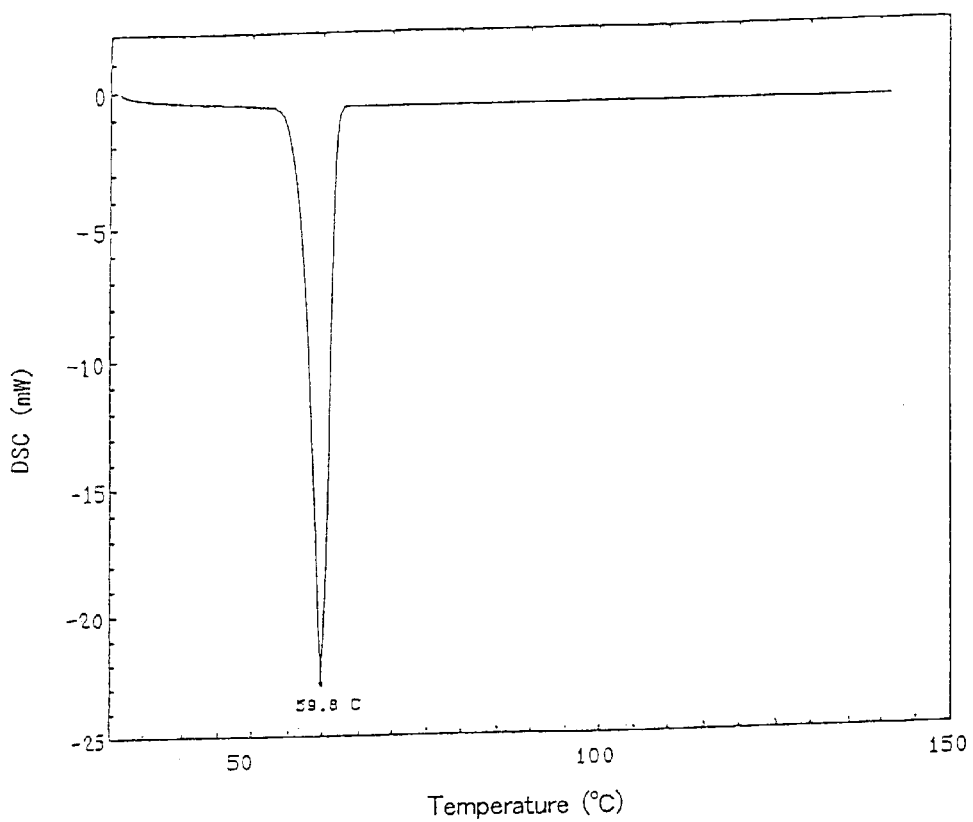
FIG. 10 is a chart showing a differential thermal curve of an ester wax obtained in Example 9.
Figure 11:
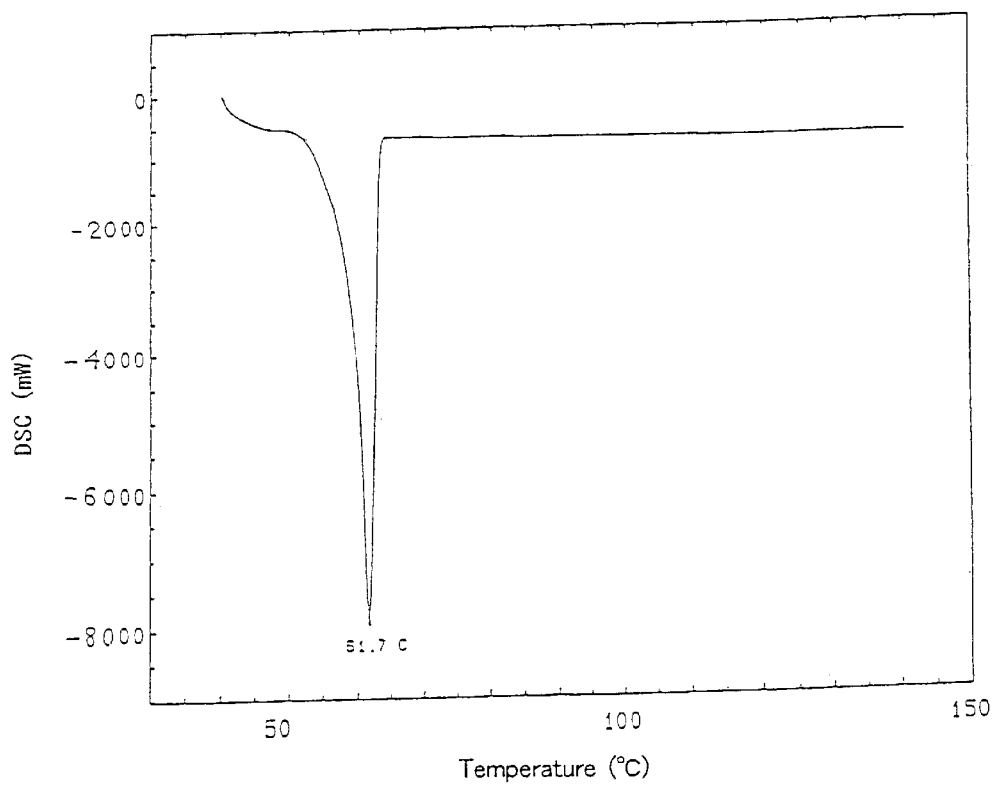
FIG. 11 is a chart showing a differential thermal curve of an ester wax obtained in Example 10.
Figure 12:
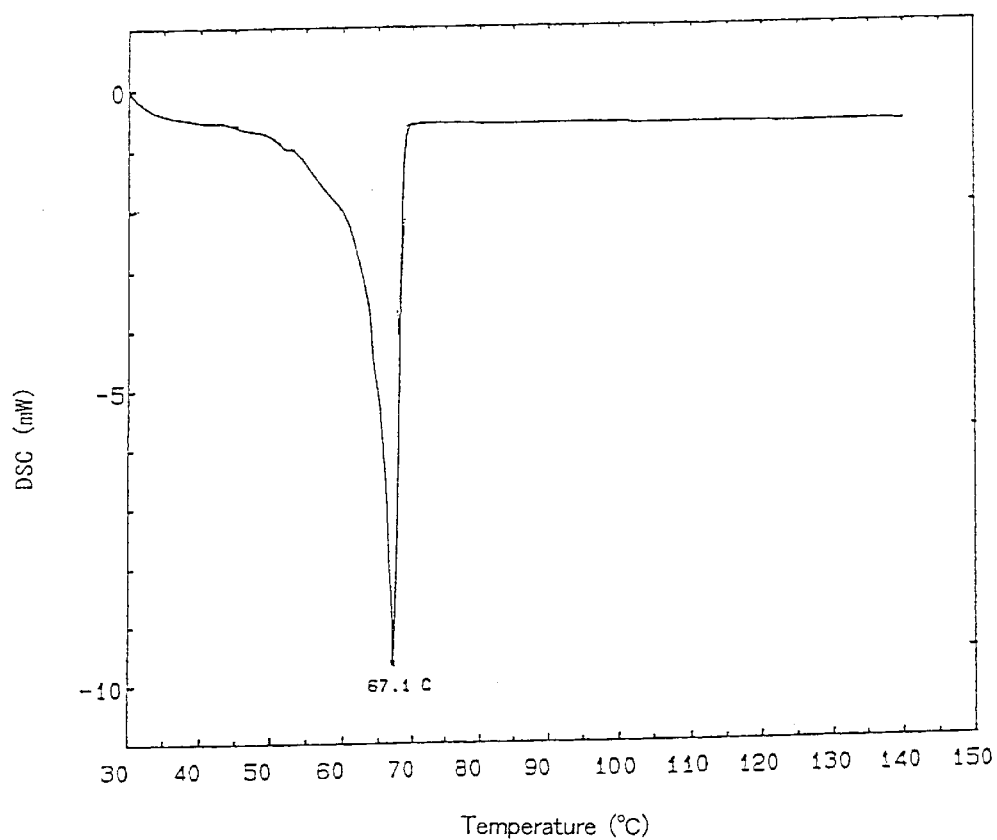
FIG. 12 is a chart showing a differential thermal curve of an ester wax obtained in Example 11.
Figure 19:
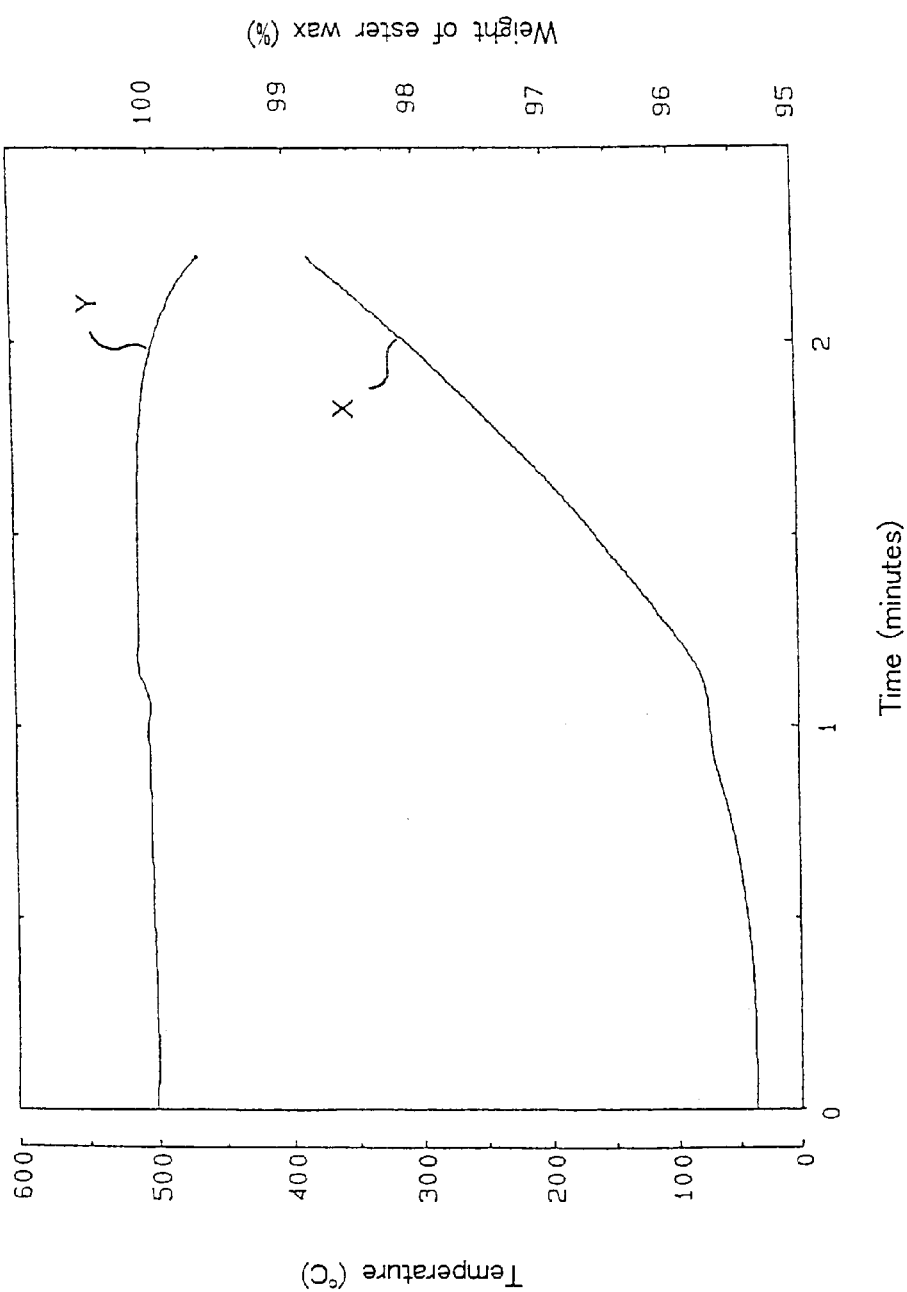
FIG. 19 is a chart obtained by thermogravimetry (TG) in Example 1.

The ester wax obtained in this example was tested by the above-described method to examine the acid value, the hydroxyl value, the color number, the viscosity, and the characteristics in the differential thermal curve. Table 2 shows the results. FIG. 4 shows the results of the differential thermal analysis of the ester wax obtained in this example. FIG. 19 shows the results of the thermogravimetry. In FIG. 19, curve X indicates the temperature in the measuring apparatus, and curve Y indicates a change (%) in the weight of the ester wax. The same applies to FIGS. 20 to 22.

Examples 2 to 11

Ester waxes were produced by the use of the carboxylic acid and the alcohol shown in Table 1 in the same manner as in Example 1. The ester waxes in Examples 5 and 6 were prepared in the same manner as in Example 4, but neither of xylene (hydrocarbon solvent: solvent I) nor ethanol was used during neutralization, and ethylene glycol (Example 5) and propylene glycol (Example 6) were used as the water-soluble organic solvent (solvent II). The obtained ester wax was tested in the same manner as in Example 1. Table 2 shows the results.

Figure 20:
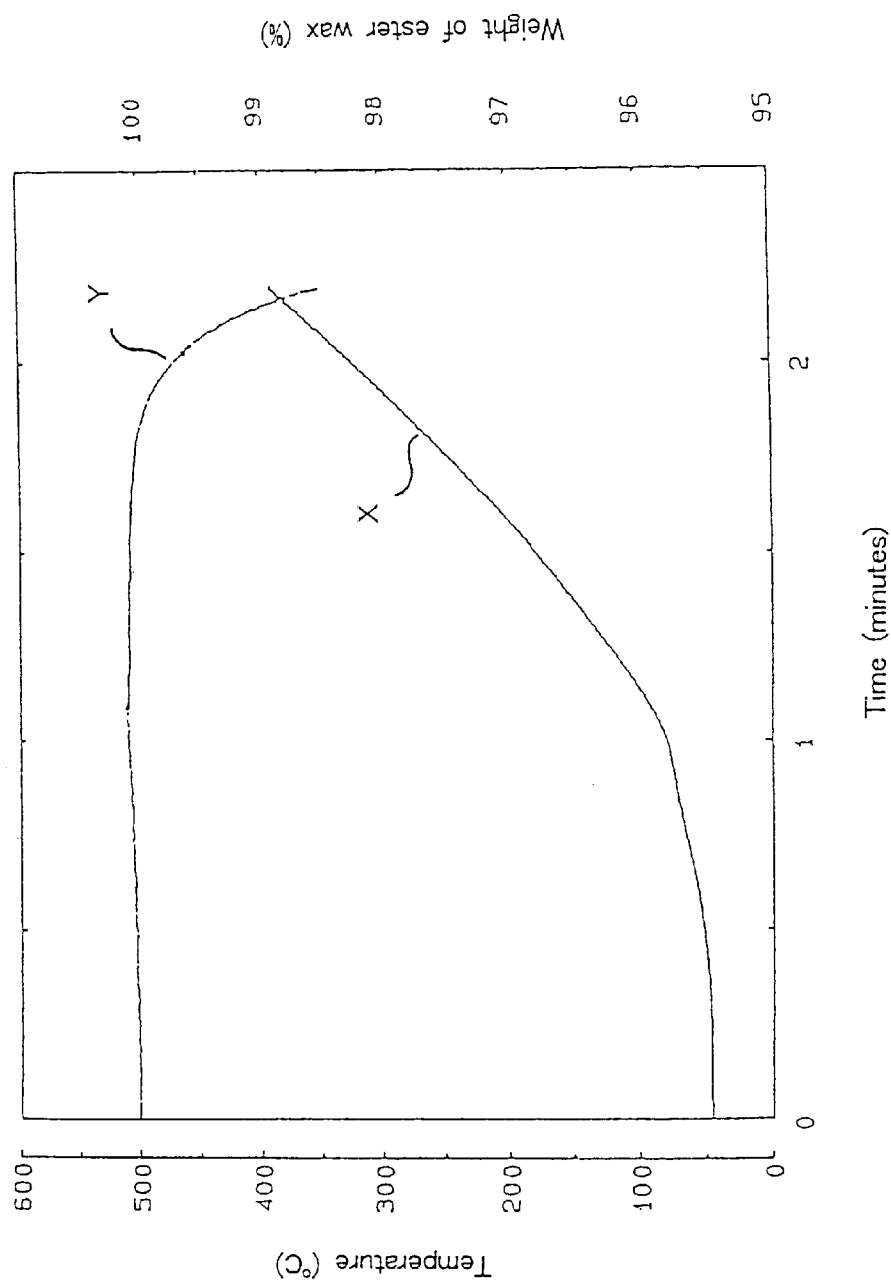
FIG. 20 is a chart obtained by thermogravimetry (TG) in Example 3.

The results of the differential thermal analysis in Examples 2 to 4 and 7 to 11 are shown in FIGS. 5 to 12, respectively. The results of the thermogravimetry of Example 3 are shown in FIG. 20. Since the ester waxes obtained in Examples 5 and 6 have the same properties as those of the ester wax obtained in Example 4, the results of each test of the ester wax of Example 4 are shown as the representative example.

Comparative Example 1

First, 100 g (0.734 mol) of pentaerythritol and 809.1 g (3.148 mol) of palmitic acid A were placed in a four-necked flask equipped with a thermometer, a nitrogen inlet, a stirrer and a condenser. Then, a reaction was carried out at an atmospheric pressure for 15 hours at 220° C. under a nitrogen flow. After the reaction was completed, only filtration was performed and thus an ester wax was obtained in an amount of 835.4 g.

Figure 13:
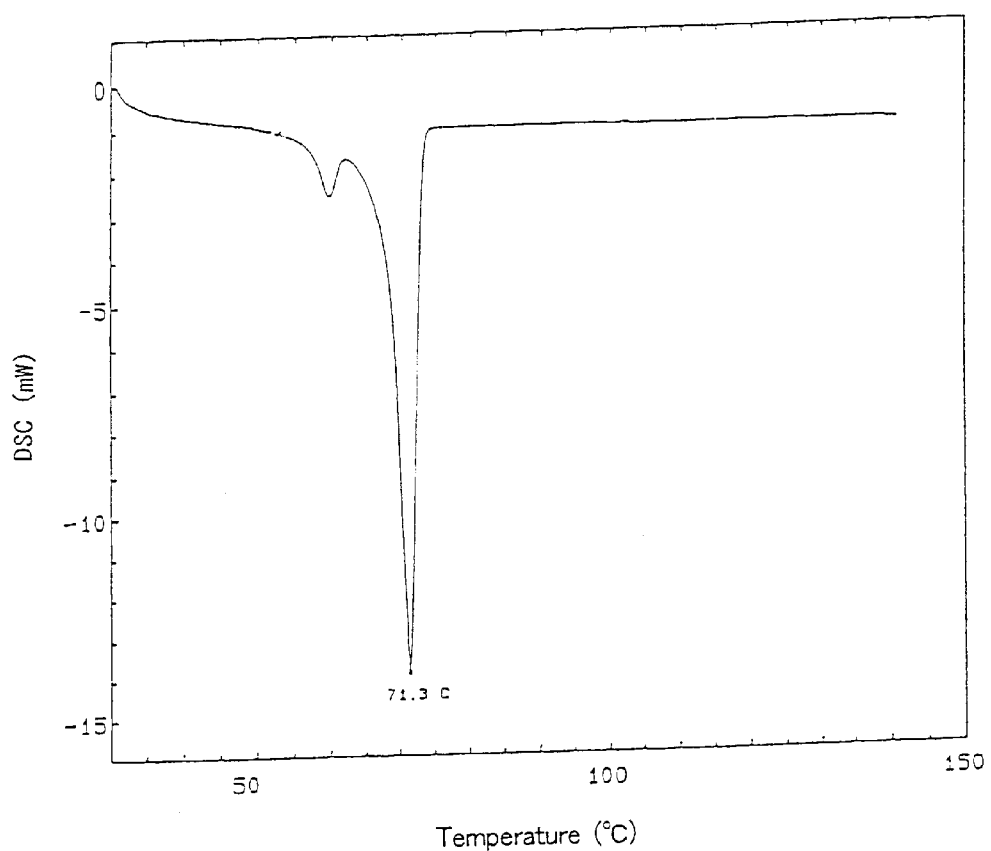
FIG. 13 is a chart showing a differential thermal curve of an ester wax obtained in Comparative Example 1.
Figure 21:
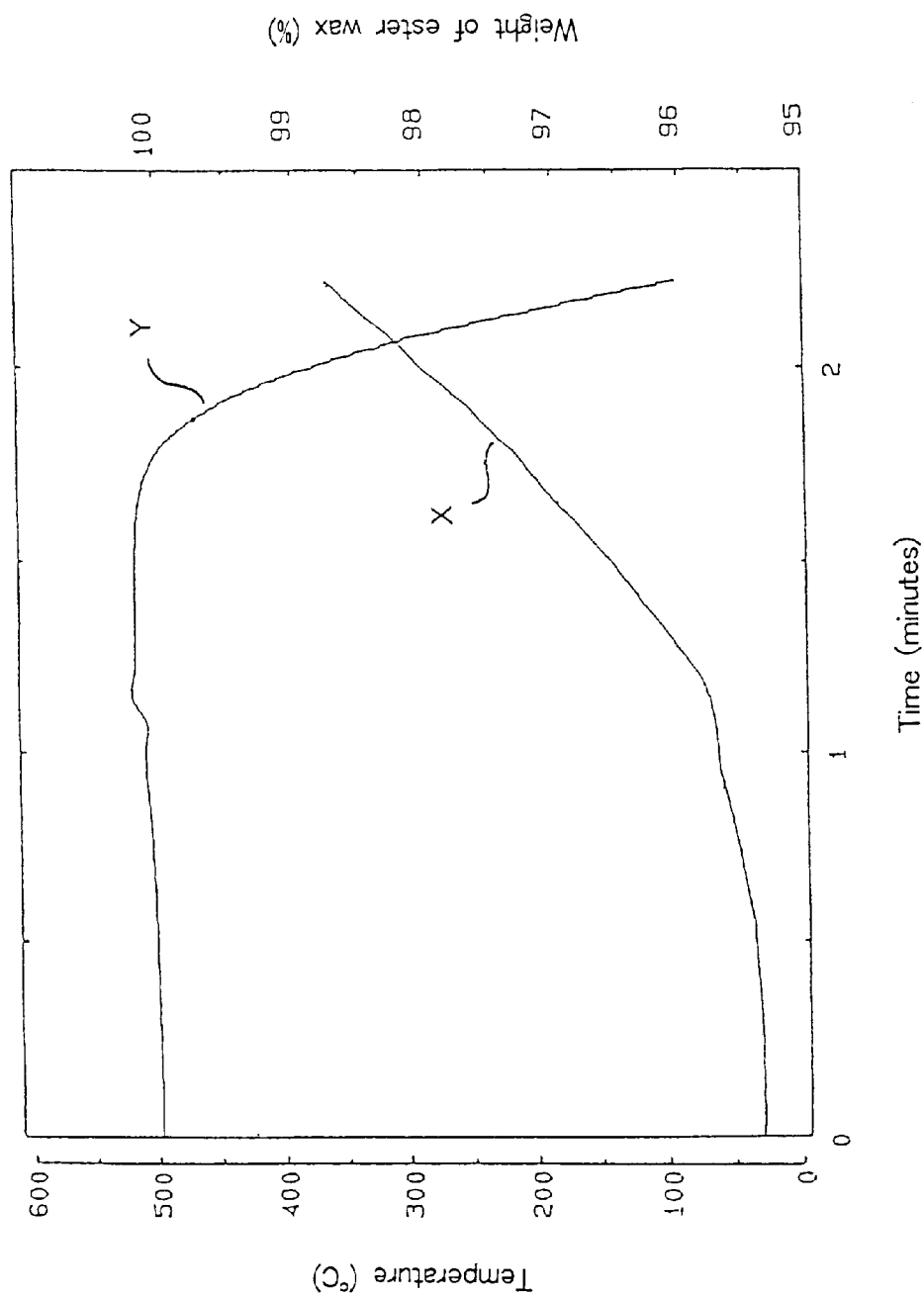
FIG. 21 is a chart obtained by thermogravimetry (TG) in Comparative Example 1.

FIG. 13 shows the results of the differential thermal analysis of the ester wax of this comparative example. FIG. 21 shows the results of the thermogravimetry.

Comparative Examples 2 and 3

Figure 14:
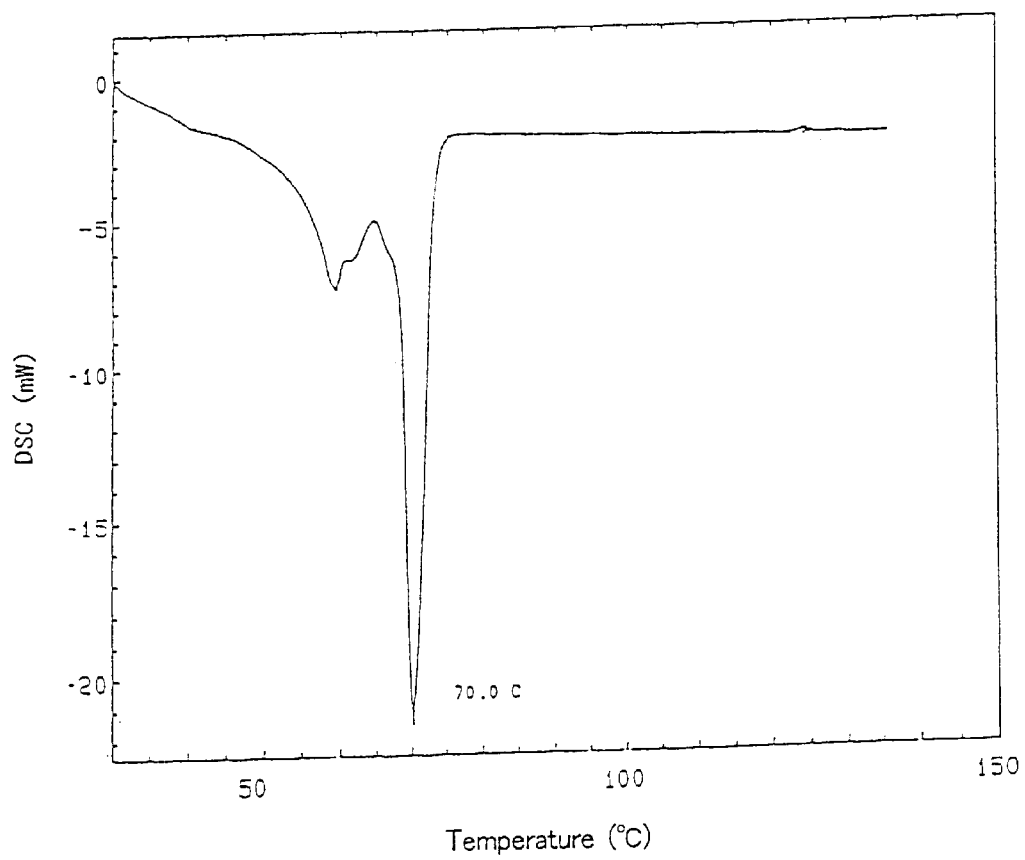
FIG. 14 is a chart showing a differential thermal curve of an ester wax obtained in Comparative Example 2.
Figure 15:
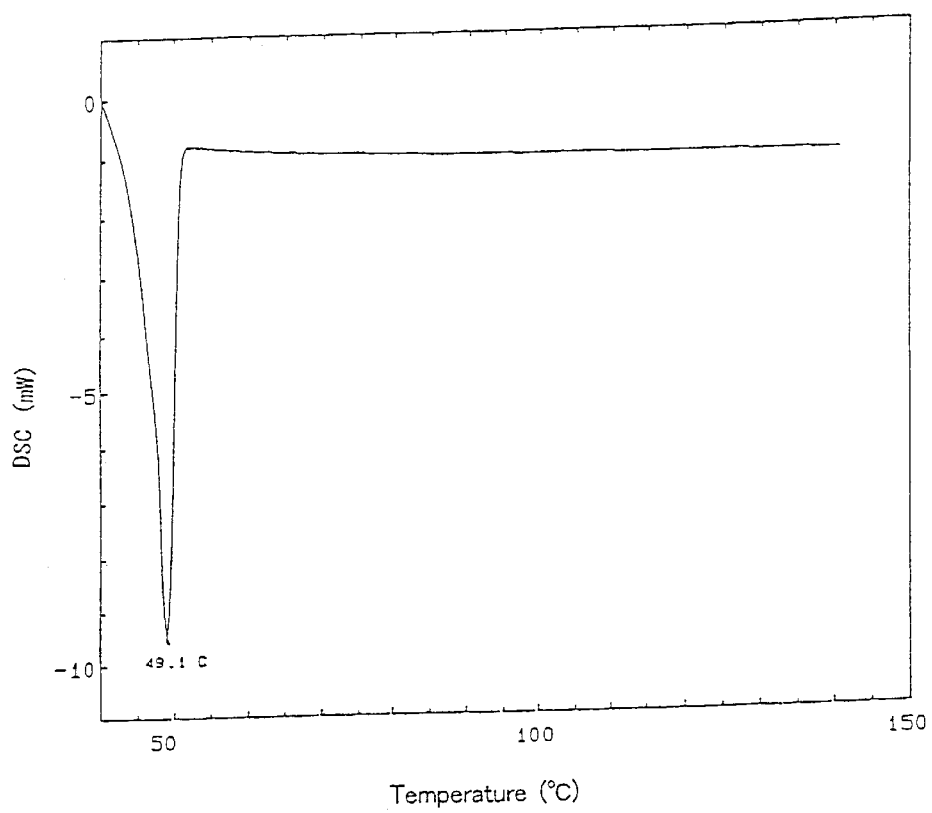
FIG. 15 is a chart showing a differential thermal curve of an ester wax obtained in Comparative Example 3.

Ester waxes were produced by the use of the carboxylic acid (component a) and the alcohol (component b) shown in Table 1 in the same manner as in Example 1. The obtained ester waxes were tested in the same manner as in Example 1. Table 2 shows the results. FIGS. 14 and 15 show the results of the differential thermal analysis of the ester waxes of Comparative Examples 2 and 3, respectively.

Comparative Examples 4 and 5

Figure 16:
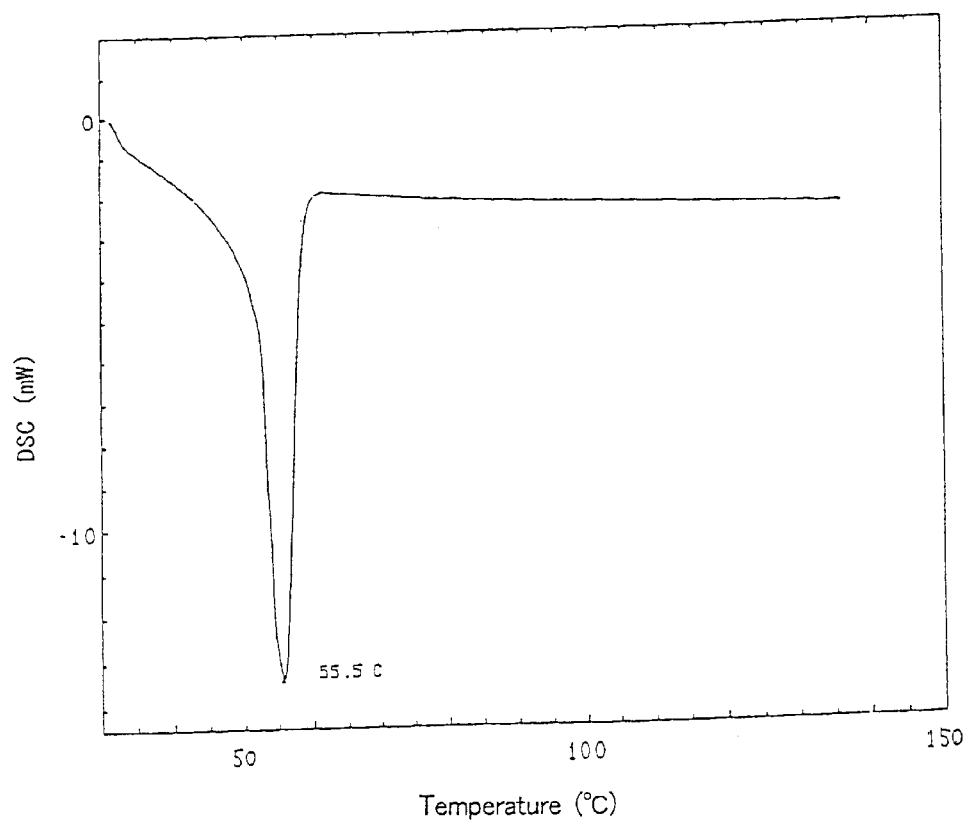
FIG. 16 is a chart showing a differential thermal curve of an ester wax obtained in Comparative Example 4.
Figure 17:
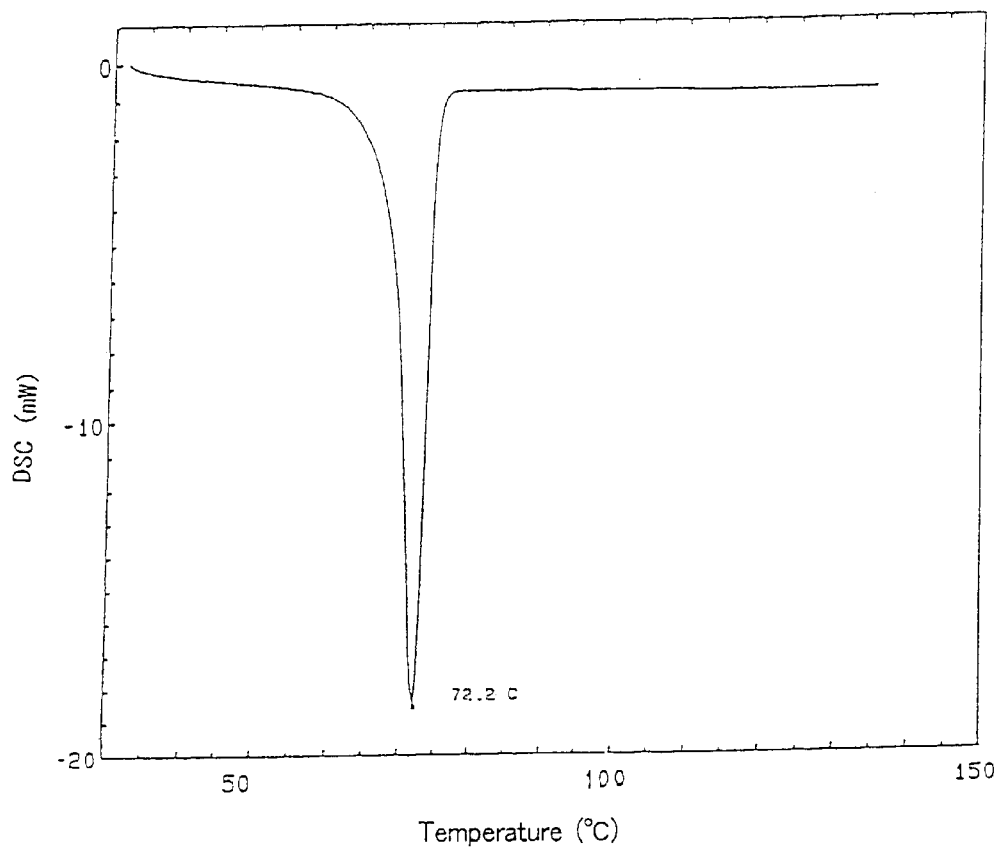
FIG. 17 is a chart showing a differential thermal curve of an ester wax obtained in Comparative Example 5.

Ester waxes were produced by the use of the carboxylic acid. (component a) and the alcohol (component b) shown in Table 1 in the same manner as in Comparative Example 1. The obtained ester waxes were tested in the same manner as in Example 1. Table 2 shows the results. FIGS. 16 and 17 show the results of the differential thermal analysis of the ester waxes of Comparative Examples 4 and 5, respectively.

Comparative Example 6

Figure 18:
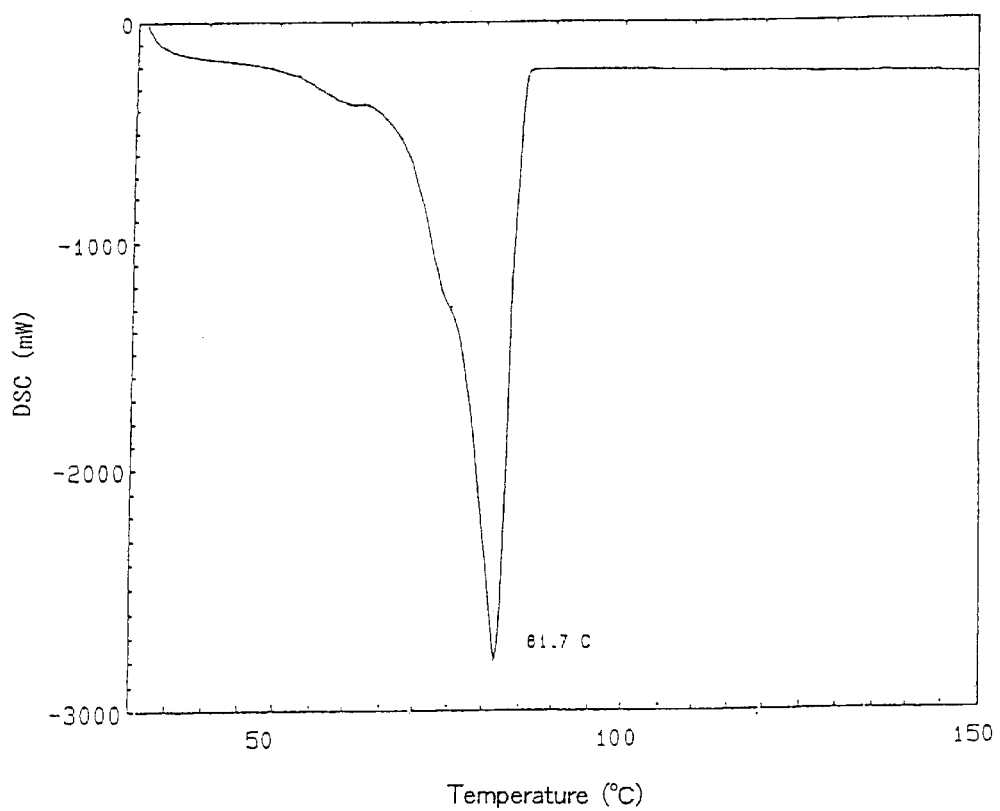
FIG. 18 is a chart showing a differential thermal curve of an ester wax obtained in Comparative Example 6.
Figure 22:
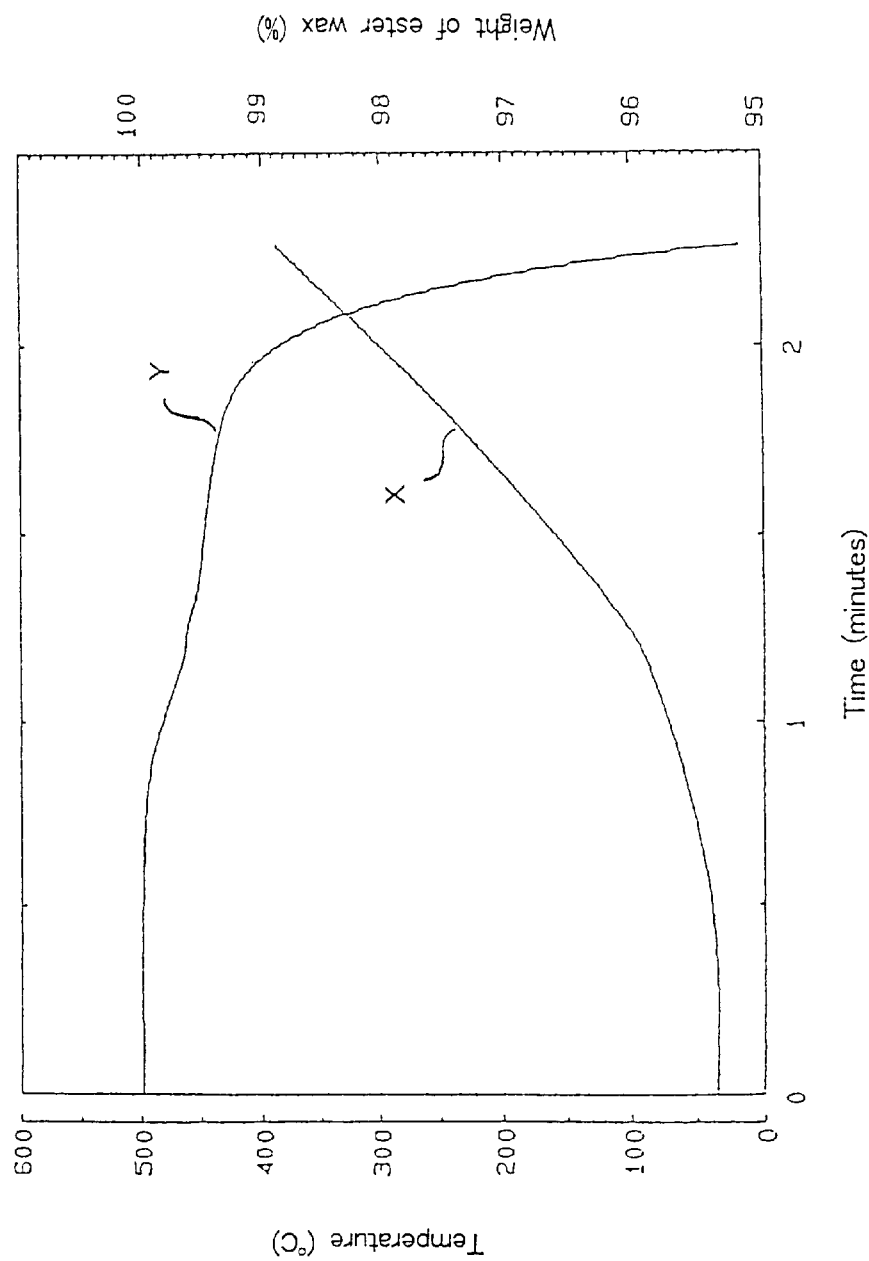
FIG. 22 is a chart obtained by thermogravimetry (TG) in Comparative Example 6.

Commercially available carnauba wax, which is a natural wax, was used as the ester wax of Comparative Example 6. FIG. 18 shows the results of the differential thermal analysis of the ester wax of Comparative Example 6. FIG. 22 shows the results of thermogravimetry.

TABLE 1

| | Materials | | | | Esterified crude product | | | | Temperature for neutralization and water-washing | Aqueous alkali solution | |
|---|---|---|---|---|---|---|---|---|---|---|---|
| | Carboxylic acid (Component a) | | Alcohol (Component b) | | Initial ratio of COOH/OH | Hydroxyl value mgKOH/g | Hydrocarbon solvent parts by weight[1] | | Alcohol solvent parts by weight[1] | | | Separation |
| | g | mol | g | mol | | | g | g | g | g | ° C. | g | |
| Example 1 | Palmitic acid A 809 | 3.15 | Pentaerythritol 100 | 0.73 | 1.07 | 845 | 10.5 | Toluene 169 | 20 | Ethanol 53 | 6 | 70 | 10% KOH solution 133 | ○ |

TABLE 1-continued

| | Materials | | | | Initial ratio of COOH/ OH | Esterified crude product | | Hydrocarbon solvent | | Alcohol solvent | | Temperature for neutralization and water-washing °C. | Aqueous alkali solution g | Separation |
| | Carboxylic acid (Component a) | | Alcohol (Component b) | | | Hydroxyl value mgKOH/ g | | | | | | | | |
| | g | mol | g | mol | | | g | g | parts by weight[1] | g | parts by weight[1] | | | |
| Example 2 | Behenic acid 451 | 1.34 | Behenyl alcohol 400 | 1.27 | 1.05 | 831 | 8.7 | Toluene 169 | 20 | Isopropanol 32 | 4 | 70 | 10% KOH solution 108 | ○ |
| Example 3 | Stearic acid A 900 | 3.16 | Pentaerythritol 100 | 0.73 | 1.07 | 950 | 12.1 | Xylene 300 | 32 | Ethanol 86 | 9 | 75 | 10% KOH solution 172 | ○ |
| Example 4 | Behenic acid 1041 | 3.08 | Pentaerythritol 100 | 0.73 | 1.05 | 1080 | 7.5 | Xylene 162 | 15 | Ethanol 42 | 4 | 80 | 10% KOH solution 120 | ○ |
| Example 5 | Behenic acid 1041 | 3.08 | Pentaerythritol 100 | 0.73 | 1.05 | 1076 | 7.7 | — | — | Ethylene glycol[2] 150 | 14 | 90 | 10% KOH solution 120 | ○ |
| Example 6 | Behenic acid 1041 | 3.08 | Pentaerythritol 100 | 0.73 | 1.05 | 1065 | 7.4 | — | — | Propylene glycol[2] 150 | 14 | 90 | 10% KOH solution 120 | ○ |
| Example 7 | Myristic acid 567 | 2.48 | Dipentaerythritol 100 | 0.39 | 1.05 | 625 | 11.1 | Toluene 187 | 30 | n-Propanol 31 | 5 | 70 | 8% NaOH solution 104 | ○ |
| Example 8 | Palmitic acid A 900 | 3.51 | Glycerin 100 | 1.09 | 1.08 | 940 | 13.8 | Cyclohexane 235 | 25 | n-Propanol 78 | 8 | 70 | 8% NaOH solution 195 | ○ |
| Example 9 | Stearic acid A 433 | 1.52 | Stearyl alcohol 400 | 1.48 | 1.03 | 802 | 5.2 | Cyclohexane 200 | 25 | Isopropanol 40 | 5 | 70 | 8% NaOH solution 63 | ○ |
| Example 10 | Stearic acid B 900 | 3.33 | Glycerin 100 | 1.09 | 1.02 | 940 | 6.3 | Toluene 188 | 120 | Ethanol 94 | 10 | 70 | 8% NaOH solution 89 | ○ |
| Example 11 | Palmitic acid B 779 | 3.08 | Pentaerythritol 100 | 0.73 | 1.06 | 828 | 10.8 | Toluene 160 | 19 | Ethanol 54 | 7 | 75 | 10% KOH solution 134 | ○ |
| Com. Ex. 1 | Palmitic acid A 809 | 3.16 | Pentaerythritol 100 | 0.73 | 1.07 | 835 | 5.8 | — | — | — | — | — | — | — |
| Com. Ex. 2 | Palmitic acid A 669 | 2.61 | Pentaerythritol 100 | 0.73 | 0.90 | 725 | 2.1 | Toluene 110 | 15 | Ethanol 36 | 5 | 70 | 10% KOH solution 23 | ○ |
| Com. Ex. 3 | Palmitic acid C 733 | 3.15 | Pentaerythritol 100 | 0.73 | 1.07 | 782 | 10.2 | Toluene 156 | 20 | Ethanol 39 | 5 | 70 | 10% KOH solution 120 | ○ |
| Com. Ex. 4 | Stearic acid A 433 | 1.52 | Stearyl alcohol 400 | 1.48 | 1.03 | 807 | 5.4 | — | — | — | — | — | — | — |
| Com. Ex. 5 | Behenic acid 451 | 1.34 | Behenyl alcohol 400 | 1.27 | 1.05 | 830 | 11.5 | — | — | — | — | — | — | — |

[1]Parts by weight per 100 parts by weight of an esterified crude product
[2]Water-soluble organic solvent (solvent II)

TABLE 2

| | Materials | | Acid value (mg KOH/g) | Hydroxyl value (mg KOH/g) | APHA color number | Viscosity (mPa · s) |
| | Carboxylic acid (Component a) | Alcohol (Component b) | | | | |
| Example 1 | Palmitic acid A | Pentaerythritol | 0.2 | 0.8 | 120 | 13.3 |
| Example 2 | Behenic acid | Behenyl alcohol | 0.1 | 0.5 | 100 | 9.1 |
| Example 3 | Stearic acid A | Pentaerythritol | 0.2 | 1.6 | 90 | 15.1 |
| Example 4 | Behenic acid | Pentaerythritol | 0.2 | 1.6 | 110 | 23.1 |
| Example 7 | Myristic acid | Dipentaerythritol | 0.2 | 1.4 | 100 | 18.3 |
| Example 8 | Palmitic acid A | Glycerin | 0.3 | 1.4 | 100 | 17.2 |
| Example 9 | Stearic acid A | Stearyl alcohol | 0.3 | 1.7 | 90 | 8.4 |
| Example 10 | Stearic acid B | Glycerin | 0.3 | 1.5 | 100 | 21.0 |
| Example 11 | Palmitic acid B | Pentaerythritol | 0.1 | 1.5 | 110 | 15.0 |
| Com. Ex. 1 | Palmitic acid A | Pentaerythritol | 5.8 | 1.0 | 120 | 12.4 |
| Com. Ex. 2 | Palmitic acid A | Pentaerythritol | 1.1 | 14.8 | 120 | 13.7 |
| Com. Ex. 3 | Palmitic acid C | Pentaerythritol | 0.2 | 0.2 | 160 | 12.2 |
| Com. Ex. 4 | Stearic acid A | Stearyl alcohol | 5.4 | 1.3 | 140 | 9.6 |

TABLE 2-continued

| | | | | | |
|---|---|---|---|---|---|
| Com. Ex. 5 | Behenic acid | Behenyl alcohol | 11.5 | 4.2 | 140 | 11.2 |
| Com. Ex. 6 | | Carnauba wax "No. 1" | 9.6 | 40.9 | >500 | 115.0 |

| | Maximum peak temperature (° C.) | Half band width (° C.) | Peak area in temperature range of 10° C.[1] (%) | Peak area included in the 3/4 temperature range[2] (%) | Thermal stability[3] (° C.) |
|---|---|---|---|---|---|
| Example 1 | 71.6 | 2.3 | 98.0 | 13.0 | 381 |
| Example 2 | 73.2 | 3.0 | 98.7 | 17.2 | 332 |
| Example 3 | 78.6 | 2.3 | 97.9 | 16.4 | 382 |
| Example 4 | 85.0 | 2.3 | 95.9 | 16.3 | 375 |
| Example 7 | 68.4 | 3.0 | 91.8 | 23.8 | 320 |
| Example 8 | 66.8 | 3.2 | 96.2 | 17.2 | 332 |
| Example 9 | 59.8 | 2.3 | 99.0 | 21.9 | 297 |
| Example 10 | 61.7 | 3.0 | 87.6 | 33.8 | 349 |
| Example 11 | 67.1 | 2.9 | 86.3 | 26.3 | 312 |
| Com. Ex. 1 | 71.3 | 2.9 | 85.1 | 26.2 | 260 |
| Com. Ex. 2 | 70.0 | 2.9 | 67.4 | 48.8 | 284 |
| Com. Ex. 3 | 49.1 | 3.6 | 98.0 | 43.0 | 278 |
| Com. Ex. 4 | 55.5 | 4.2 | 92.6 | 33.7 | 210 |
| Com. Ex. 5 | 72.2 | 3.5 | 94.3 | 18.7 | 258 |
| Com. Ex. 6 | 81.7 | 6.8 | 71.9 | 32.1 | 120 |

[1] Ratio of the peak area in the 10° C. range between the maximum peak temperature minus 7° C. and the maximum peak temperature plus 3° C. to the total peak area in the differential thermal curve
[2] Ratio of the peak area corresponding to the temperature region of 3/4 on the low temperature side of the peak area in the range from the melting start temperature to the maximum peak temperature to the total peak area in the differential thermal curve
[3] Temperature at which the weight of the ester wax decreases by 0.5 wt % in thermogravimetry

TABLE 3

| | Carbon numbers and contents (wt %) of carboxylic acids or alcohols | | | | | | | | | | | | | | | |
|---|---|---|---|---|---|---|---|---|---|---|---|---|---|---|---|---|
| Materials | C3 | C5 | C10 | C12 | C14 | C16 | C18 | C20 | C22 | C24 | C26 | C28 | C30 | C32 | C34 | C36 |
| Palmitic acid A | | | | | 1 | 96 | 3 | | | | | | | | | |
| Palmitic acid B | | | | | 15 | 85 | | | | | | | | | | |
| Palmitic acid C | | | | 35 | 15 | 50 | | | | | | | | | | |
| Myristic acid | | | | 2 | 98 | | | | | | | | | | | |
| Stearic acid A | | | | | | 2 | 98 | | | | | | | | | |
| Stearic acid B | | | 1 | 1 | 4 | 30 | 64 | | | | | | | | | |
| Behenic acid | | | | | | | 1 | 10 | 87 | 2 | | | | | | |
| Stearyl alcohol | | | | | | | 98 | | | | | | | | | |
| Behenyl alcohol | | | | | | | 15 | 16 | 68 | 1 | | | | | | |
| Pentaerythritol | | 100 | | | | | | | | | | | | | | |
| Dipentaerythritol | | 1 | 99 | | | | | | | | | | | | | |
| Glycerin | 100 | | | | | | | | | | | | | | | |
| Carnauba wax "No. 1" | | | | | | | | | | | | | | | | |
| Carboxylic acid component | | | | 4 | 5 | 13 | 12 | 27 | 14 | 18 | 5 | 2 | | | | |
| Alcohol component | | | | | | | | | 2 | 3 | 2 | 4 | 13 | 56 | 19 | 3 |

As seen from Table 2, for all the ester waxes of Examples 1 to 11, the acid value is 3.0 mgKOH/g or less, the hydroxyl value is 5.0 mgKOH/g or less, the color number (APHA) is 300 or less, and the viscosity (melt viscosity at 100° C.) is 120 mPa·s or less. For these ester waxes, the maximum peak temperatures are in the temperature range from 55 to 90° C., and the half band width of the maximum peak is 5° C. or less. Furthermore, 80% or more of the total peak area lies in the 10° C. range between the maximum peak temperature minus 7° C. and the maximum peak temperature plus 3° C., and the peak area corresponding to the temperature range of ¾ on the lower temperature side of the peak area in the range from the melting start temperature to the maximum peak temperature is 35% or less. Such ester waxes have sharp melting characteristics. When these ester waxes are heated at 250° C./min for 2 minutes, the temperature at which the weight decrease due to heating reaches 0.5 wt % is 290° C. or more for all the ester waxes, and thus the thermal stability is good.

On the other hand, regarding the comparative examples, the ester waxes of Comparative Examples 1, 4 and 5 have a high acid value, and the ester wax of Comparative Example 2 has a high hydroxyl value. In Comparative Example 6, the acid value is as high as 9.6 mgKOH/g, and the hydroxyl value is as high as 40.9 mgKOH/g. In addition, the color number (APHA) is as high as more than 500. In the heat characteristics determined by DSC, Comparative Example 3 employs a low purity carboxylic acid, so that the maximum peak temperature of the resultant ester is lower than 55° C., and in Comparative Example 6, the half band width is larger than 5° C. In Comparative Examples 2 and 6, the peak area in the temperature range of 10° C. including the maximum peak temperature is less than 80%. In the ester waxes of Comparative Examples 2 and 3, the peak area in the temperature range of ¾ on the lower temperature side of the peak area in the range from the melting start temperature to the maximum perk temperature exceeds 35%. Thus, none of the ester waxes obtained in the comparative examples has sharp melting characteristics. Moreover, for all the ester waxes of the comparative examples, the temperature at which the weight decrease due to heating reaches 0.5 wt % is less than 290° C., and thus the thermal stability is poor.

II. Production and Evaluation of Toner

Example 12

First, 95 parts of polyester resin (softening point of 85° C.), 6 parts of the ester wax obtained in Example 1, 8 parts of carbon black, and 3 parts of nigrosine dye were melted and mixed by high speed stirring. After the resultant mixture was cooled to room temperature, the mixture was pulverized roughly with a hammer mill, and then pulverized to fine powder with a pulverizer of air jet milling. The resultant finely pulverized product was classified with a pneumatic classifier to obtain an average particle size of 9 $\mu$m. To 100 parts of the particles, one part of fine powder of titanium oxide (average particle size of 0.02 $\mu$m) as a lubricant was added and mixed, so that a one-component magnetic toner "T-1" was obtained. Thereafter, using the ester waxes obtained in Examples 2 and 4 in amounts shown in Table 4, the same operations as above were performed so that one-component system magnetic toners "T-2", "T-3", "T-4" and "T-5" were obtained.

The obtained toners were subjected to the above-described test for evaluation of the storage stability and the OHP optical transparency. Furthermore, the fixing properties during copying, the presence or the absence of offset, and the occurrence of filming during copying, were evaluated by the above-described test methods. Table 4 shows the results.

Comparative Example 7

Toners "T-16", "T-17", and "T-18" shown in Table 4 were obtained in the same manner as in Example 12, except that the ester wax obtained in Example 1 was replaced by the ester waxes obtained in Comparative Examples 1, 2 and 3, respectively. The obtained toners were tested in the same manner as in Example 12. Table 4 shows the results.

Example 13

An aqueous dispersion containing a magnesium hydroxide colloid was prepared by placing an aqueous solution containing 10 parts of magnesium chloride dissolved in 250 parts of ion exchanged water, and adding an aqueous solution containing 7 parts of sodium hydroxide dissolved in 57 parts of ion exchanged water thereto gradually under stirring.

Separately, 100 parts of a monomer composition comprising 60 parts of styrene monomer and 40 parts of n-butyl acrylate monomer, 5 parts of carbon black, one part of a charge controlling agent ("Spiron Black TRH" manufactured by Hodogaya Chemical Co., Ltd.), 0.3 parts of divinyl benzene, 0.5 parts of polymethacrylic acid ester macromonomer ("AA6" manufactured by Toagosei Co., Ltd.), 5 parts of the ester wax obtained in Example 3 and 2 parts of 2,2-azobis isobutyronitrile were placed in a four-necked flask equipped with a TK type homomixer capable of mixing at a high shearing force. Then, the mixture was stirred and mixed at 6000 rpm for homogenous dispersion, so that a mixture containing the monomers was obtained. This mixture was fed into the aqueous dispersion and the resultant mixture was stirred with a TK type homomixer at 8000 rpm for 20 minutes at a high shearing force for granulation. The aqueous dispersion including the granulated monomer-containing mixture was placed in a reaction vessel with a stirring blade instead of a stirrer. The aqueous dispersion was stirred at 250 rpm for 10 hours while the internal temperature was maintained at 65° C. for polymerization. Thus, an aqueous dispersion containing polymer particles was obtained. After the polymerization was completed, the aqueous dispersion was cooled to 25° C., washed with diluted sulfuric acid for 10 minutes, and then was filtrated off to remove water. Thereafter, 500 parts of ion exchanged water were added to form a slurry again and the slurry was washed with water. Again, removal of water and water-washing were repeated several times, and a solid was filtrated off and separated, and then drying was performed in a hot air dryer at 50° C. for a whole day and night. Thus, polymerized particles were obtained.

To 100 parts of the obtained polymer particles, 0.3 parts of colloidal silica ("R-972" manufactured by Nippon Aerosil Co., Ltd.) that had been treated to be provided with hydrophobicity were added and mixed with a Henschel mixer to prepare a polymerized toner. To 5 parts of the obtained toner, 100 parts of ferrite beads coated with silicone (manufactured by Powder Tech) were mixed, and this mixture was denoted by "T-6" as a two-component system toner. Thereafter, the same operations as above were performed by the use of the ester waxes obtained in Examples 4 and 5, so that polymerized toners "T-7" and "T-8" were obtained, respectively. The obtained toners were tested in the same manner as in Example 12. Table 4 shows the results.

Comparative Example 8

Toners "T-19", "T-20", and "T-21" were obtained in the same manner as in Example 13, except that the ester wax obtained in Example 3 was replaced by the ester waxes obtained in Comparative Examples 1, 4 and 5, respectively. The obtained toners were tested in the same manner as in Example 12. Table 4 shows the results.

Example 14

First, 94 parts of dimethyl terephthalate, 95 parts of dimethyl isophthalate, 89 parts of ethylene glycol, 80 parts of neopentyl glycol, and 0.1 parts of zinc acetate were fed in an autoclave equipped with a thermometer and a stirrer, and the mixture was heated at 120 to 230° C. for 120 minutes to effect an ester exchange reaction. Then, 8.4 parts of 5-sodium sulfoisophthalic acid was added to the mixture and the reaction was further continued at 220 to 230° C. for 60 minutes, After the mixture was further heated to 250° C., the reaction continued for further 60 minutes at a system pressure of 1 to 10 mmHg. As a result, a copolymerized polyester emulsion was obtained. To one liter of this emulsion, 30 mL of emulsion (solid content of 30%) of the ester wax of Example 4 was added. The obtained mixture was subjected to a granulation operation by being dropped to 2 L of a MgSO$_4$ (0.2%) aqueous solution that had been heated to 40° C. over about 30 minutes while being sufficiently stirred. The resultant mixture was kept at this temperature for further 30 minutes and cooled to room temperature. Then, 100 g of an aqueous dispersion of the resultant polyester resin particles (including an ester as a releasing agent), and 3 g of C.I. Disperse Yellow 64 as a dye (yellow) were fed in a stainless steel pot, and heated from room temperature to 130° C. at a heating rate of 3° C./min, and kept at 130° C. for 60 minutes, and then cooled to room temperature. The resultant dyed particles were filtrated, washed, and dried with a spray dryer, and thus resin particles that were colored yellow were obtained.

Thereafter, resin particles that had been colored magenta and cyan were obtained in the same manner as above by the use of C.I. Disperse Red 92 for magenta and C.I. Disperse Blue 60 for cyan, respectively. To 100 g of the resultant dyed resin particles, 1 g of silica was mixed, and thus yellow toner, magenta toner and cyan toner were obtained. Then, 100 g of ferrite beads coated with silicone were mixed with 5 g each of the yellow toner, the magenta toner and the cyan toner. This is denoted by "T-9" as a two-component system toner. Thereafter, polymerized toners "T-10", "T-11", "T-12" and "T-13" were obtained by the use of the ester waxes of Examples 8, 9, 10 and 11 by the same operations as above. Furthermore, a polymerized toner "T-14" was prepared in the same manner as mentioned above except that a mixture of the ester wax of Example 1 and the ester wax of Example 3 was used in such a manner that each ester wax was contained in an amount of 5 wt % in the toner. Also, a polymerized toner "T-15" was prepared in the same manner as mentioned above except that a mixture of the ester wax of Example 8 and the ester wax of Example 10 was used in such a manner that the ester waxes were contained in amounts of 3 wt % and 5 wt %, respectively, in the toner. The obtained toners were tested in the same manner as in Example 12. Table 4 shows the results.

Comparative Example 9

Toners "T-22" and "T-23" were obtained in the same manner as in Example 14, except that the ester wax obtained in Example 4 was replaced by the ester waxes obtained in Comparative Examples 1 and 6, respectively. The obtained toners were tested in the same manner as in Example 12. Table 4 shows the results.

The toners "T-1" to "T-15" shown in Table 4 provided vivid images with a high quality density and without stains or offset stains on the resultant copied sheets. The storage stability and the OHP optical transparency were good and there was no offset. When it was examined whether or not filming occurred, no filming occurred even in the 50,000th copy, and vivid images with a high quality density and without stains on the resultant copied sheets were obtained.

On the other hand, when the toner "T-16" to "T-23" containing the ester waxes of the comparative examples were used, filming occurred in the 50,000th running test, the copied sheet surfaces were stained and the image density was low, and thus only images that are not suitable for practical use were obtained.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. An ester wax obtained by a condensation reaction of carboxylic acid and alcohol, wherein the carboxylic acid contains a single kind of saturated linear monocarboxylic acid having 14 to 30 carbon atoms as a main component, and the single kind of carboxylic acid is contained in a ratio of 60 wt % or more of the entire carboxylic acid, the alcohol contains a single kind of saturated linear monohydric alcohol having 14 to 30 carbon atoms or a single kind of polyhydric alcohol having 2 to 6 hydroxyl groups and having 2 to 30 carbon atoms as a main component, and when the monohydric alcohol is

TABLE 4

| Toner (ester wax used; content of ester) | Storage stability | OHP optical transparency | Fixing properties | Offset | Filming[3] |
|---|---|---|---|---|---|
| T-1 (ester wax in Example 1; 5 wt %) | ○ | ○ | ○ | Absent | Absent |
| T-2 (ester wax in Example 2; 1 wt %) | ○ | ○ | ○ | Absent | Absent |
| T-3 (ester wax in Example 2; 8 wt %) | ○ | ○ | ○ | Absent | Absent |
| T-4 (ester wax in Example 2; 15 wt %) | ○ | ○ | ○ | Absent | Absent |
| T-5 (ester wax in Example 4; 10 wt %) | ○ | ○ | ○ | Absent | Absent |
| T-6 (ester wax in Example 3; 4 wt %) | ○ | ○ | ○ | Absent | Absent |
| T-7 (ester wax in Example 4; 5 wt %) | ○ | ○ | ○ | Absent | Absent |
| T-8 (ester wax in Example 7; 10 wt %) | ○ | ○ | ○ | Absent | Absent |
| T-9 (ester wax in Example 4; 8 wt %) | ○ | ○ | ○ | Absent | Absent |
| T-10 (ester wax in Example 8; 10 wt %) | ○ | ○ | ○ | Absent | Absent |
| T-11 (ester wax in Example 9; 5 wt %) | ○ | ○ | ○ | Absent | Absent |
| T-12 (ester wax in Example 10; 5 wt %) | ○ | ○ | ○ | Absent | Absent |
| T-13 (ester wax in Example 11; 5 wt %) | ○ | ○ | ○ | Absent | Absent |
| T-14 (mixture[1]) | ○ | ○ | ○ | Absent | Absent |
| T-15 (mixture[2]) | ○ | ○ | ○ | Absent | Absent |
| T-16 (ester wax in Com. Ex. 1; 5 wt %) | × | ○ | ○ | Absent | Present |
| T-17 (ester wax in Com. Ex. 2; 5 wt %) | × | ○ | × | Present | Present |
| T-18 (ester wax in Com. Ex. 3; 8 wt %) | × | ○ | × | Present | Present |
| T-19 (ester wax in Com. Ex. 1; 3 wt %) | × | ○ | ○ | Present | Present |
| T-20 (ester wax in Com. Ex. 4; 5 wt %) | × | ○ | × | Present | Present |
| T-21 (ester wax in Com. Ex. 5; 5 wt %) | × | ○ | ○ | Present | Present |
| T-22 (ester wax in Com. Ex. 1; 5 wt %) | × | ○ | ○ | Present | Present |
| T-23 (ester wax in Com. Ex. 6; 5 wt %) | × | × | ○ | Present | Present |

[1] Mixture of the ester wax of Example 1 and the ester wax of Example 3 (5 wt % each)
[2] Mixture of the ester wax of Example 8 and the ester wax of Example 10 (3 wt % and 5 wt %, respectively)
[3] Filming at the time when 50,000 copies were made the main component, the monohydric alcohol is contained in a ratio of 60 wt % or more of the entire alcohol, and when the polyhydric alcohol is the main component, the polyhydric alcohol is contained in a ratio of 80 wt % or more of the entire alcohol, and the ester wax has an acid value of 3 mgKOH/g or less and a hydroxyl value of 5 mgKOH/g or less, and a maximum peak temperature in a differential thermal curve is in a range from 55° C. to 90° C.

2. The ester wax according to claim 1, wherein 80% or more of a total peak area lies in a 10° C. range between the maximum peak temperature minus 7° C. and the maximum peak temperature plus 3° C. in the differential thermal curve.

3. The ester wax according to claim 2, wherein a peak area corresponding to a temperature region of ¾ on the low temperature side of a peak area in a range from a melting start temperature to the maximum peak temperature in the differential thermal curve is 35% or less of the total peak area.

4. The ester wax according to claim 2, wherein a half band width of the maximum peak is 50° C. or less.

5. A toner comprising 100 parts by weight of a binding resin and 0.1 to 40 parts by weight of the ester wax according to claim 2.

6. The ester wax according to claim 1, wherein a peak area corresponding to a temperature region of ¾ on the low temperature side of a peak area in a range from a melting start temperature to the maximum peak temperature in the differential thermal curve is 35% or less of the total peak area.

7. The ester wax according to claim 6, wherein a half band width of the maximum peak is 50° C. or less.

8. A toner comprising 100 parts by weight of a binding resin and 0.1 to 40 parts by weight of the ester wax according to claim 6.

9. The ester wax according to claim 1, wherein a half band width of the maximum peak is 5° C. or less.

10. A toner comprising 100 parts by weight of a binding resin and 0.1 to 40 parts by weight of the ester wax according to claim 9.

11. A toner comprising 100 parts by weight of a binding resin and 0.1 to 40 parts by weight of the ester wax according to claim 1.

12. An ester wax obtained by a process comprising a condensation reaction of carboxylic acid and alcohol, wherein the carboxylic acid contains a single kind of saturated linear monocarboxylic acid having 14 to 30 carbon atoms as a main component, and the single kind of carboxylic acid is contained in a ratio of 60 wt % or more of the entire carboxylic acid, the alcohol contains a single kind of saturated linear monohydric alcohol having 14 to 30 carbon atoms or a single kind of polyhydric alcohol having 2 to 6 hydroxyl groups and having 2 to 30 carbon atoms as a main component, and when the monohydric alcohol is the main component, the monohydric alcohol is contained in a ratio of 60 wt % or more of the entire alcohol, and when the polyhydric alcohol is the main component, the polyhydric alcohol is contained in a ratio of 80 wt % or more of the entire alcohol, and the process comprises adding a hydrocarbon solvent to an esterified crude product obtained by the condensation reaction in a ratio of 5 to 100 parts by weight with respect to 100 parts by weight of the esterified crude product, and performing neutralization with an aqueous alkali solution.

13. A toner comprising 100 parts by weight of a binding resin and 0.1 to 40 parts by weight of the ester wax according to claim 12.

14. The ester wax according to claim 12, which is obtained by a process comprising further adding an alcohol solvent having 1 to 3 carbon atoms in a ratio of 3 to 50 parts by weight with respect to 100 parts by weight of the esterified crude product, in addition to the hydrocarbon solvent, and performing neutralization with an aqueous alkali solution.

15. A toner comprising 100 parts by weight of a binding resin and 0.1 to 40 parts by weight of the ester wax according to claim 14.

16. An ester wax obtained by a process comprising a condensation reaction of carboxylic acid and alcohol, wherein the carboxylic acid contains a single kind of saturated linear monocarboxylic acid having 14 to 30 carbon atoms as a main component, and the single kind of carboxylic acid is contained in a ratio of 60 wt % or more of the entire carboxylic acid, the alcohol contains a single kind of saturated linear monohydric alcohol having 14 to 30 carbon atoms or a single kind of polyhydric alcohol having 2 to 6 hydroxyl groups and having 2 to 30 carbon atoms as a main component, and when the monohydric alcohol is the main component, the monohydric alcohol is contained in a ratio of 60 wt % or more of the entire alcohol, and when the polyhydric alcohol is the main component, the polyhydric alcohol is contained in a ratio of 80 wt % or more of the entire alcohol, and the process comprises adding a water-soluble organic solvent to an esterified crude product obtained by the condensation reaction in a ratio of 3 to 50 parts by weight with respect to 100 parts by weight of the esterified crude product, and performing neutralization with an aqueous alkali solution, wherein the water-soluble organic solvent has a boiling point that is a temperature exceeding a melting temperature of the esterified crude product but not more than 300° C., and has a specific gravity of 0.9 or more.

17. A toner comprising 100 parts by weight of a binding resin and 0.1 to 40 parts by weight of the ester wax according to claim 16.

* * * * *

UNITED STATES PATENT AND TRADEMARK OFFICE
CERTIFICATE OF CORRECTION

PATENT NO. : 6,713,221 B2
DATED : March 30, 2004
INVENTOR(S) : Kada et al.

It is certified that error appears in the above-identified patent and that said Letters Patent is hereby corrected as shown below:

Title page,
Item [56], References Cited, U.S. PATENT DOCUMENTS, add:
-- 2,958,706 A  11/1960    Hurwitz et al. --
FOREIGN PATENT DOCUMENTS, add:
-- EP   0 899 617    3/1999 --

Column 22,
Lines 50-51, "60 minutes," should read -- 60 minutes. --.

Column 25,
Lines 21 and 32, "50º C" should read -- 5º C --.

Signed and Sealed this

Seventeenth Day of August, 2004

JON W. DUDAS
*Acting Director of the United States Patent and Trademark Office*